United States Patent [19]
Gschneidner, Jr. et al.

[11] Patent Number: 5,806,979
[45] Date of Patent: Sep. 15, 1998

[54] CALORIMETRIC SYSTEM AND METHOD

[75] Inventors: Karl A. Gschneidner, Jr.; Vitalij K. Pecharsky, both of Ames; Jack O. Moorman, Boone, all of Iowa

[73] Assignee: Iowa State University Research Foundation, Inc., Ames, Iowa

[21] Appl. No.: 753,036

[22] Filed: Nov. 19, 1996

[51] Int. Cl.$^6$ .......................... G01K 17/00; G01N 25/20
[52] U.S. Cl. .................. 374/34; 374/33; 374/43; 422/51
[58] Field of Search .............................. 374/34, 33, 43; 422/51

[56] References Cited

U.S. PATENT DOCUMENTS

| | | | |
|---|---|---|---|
| 3,267,728 | 8/1966 | Solomons | 374/34 |
| 3,365,944 | 1/1968 | Hoagland | 374/34 |
| 3,813,937 | 6/1974 | Fletcher et al. | 374/34 |
| 4,185,497 | 1/1980 | Decker et al. | 374/32 |
| 4,208,907 | 6/1980 | Townsend et al. | 374/34 |
| 4,333,332 | 6/1982 | Privalov | 374/10 |
| 4,765,749 | 8/1988 | Bourgade et al. | 374/32 |
| 4,783,174 | 11/1988 | Gmelin et al. | 374/33 |
| 4,892,707 | 1/1990 | Stockton et al. | 422/51 |

FOREIGN PATENT DOCUMENTS

| | | | |
|---|---|---|---|
| 1118997 | 12/1961 | Germany | 374/34 |
| 2754275 | 6/1979 | Germany | 374/34 |
| 0712696 | 1/1980 | U.S.S.R. | 374/34 |

OTHER PUBLICATIONS

Modern Low–Temperature Calorimetry; Thermochimica Acta, 29 (1979) pp. 1–39; E. Gmelin.

Enthalpy increment measurements from 4.5 . . . Bismuth (cr). Thermodynamic Properties from 0 K to the Melting Point. J. Chem. Eng. Data 1995, 40, pp. 1015–1024; D. G. Archer.

"Tray" Type Calorimeter for the 15–300 K Temperature Range: Copper as a specific Heat Standard in This Range; Rev. Sci. Instrum. 58(4), Apr. 1987, pp. 639–646; D. L. Martin.

Apparatus For Heat Capacity Measurements of Amorphous Metals; J. Phys. E; Sci. Instrum., vol. 18, 1985, pp. 581–583; Lanchester and Mohammed.

Automated Small Sample Calorimeter; pp. 1054–1059, Schwall, Howard and Stewart.

Automatic Calorimetry in the 3–30 K Range. The Specific Heat of Copper; Sci. Instrum., vol. 44, No. 6, Jun. 1973; pp. 675–684; Martin, Bradley, Cazemier and Snowdon.

Cash, W. M. et al., "Application of a digital computer to data acquisition and shield temperature control of a high–temperature, adiabatic calorimeter," Dev. Sci. Instrum. vol. 52, No. 6, pp. 895–901 (Jun. 1981).

Moses, D. et al., "Simple calorimetric system for the temperature range 3–300 k with on–line computer," Dev. Sci. Instrum., vol. 48, No. 8, pp. 1098–1103 (Aug. 1977).

*Primary Examiner*—Diego F. F. Gutierrez
*Attorney, Agent, or Firm*—Edward J. Timmer

[57] ABSTRACT

Apparatus for measuring heat capacity of a sample where a series of measurements are taken in succession comprises a sample holder in which a sample to be measured is disposed, a temperature sensor and sample heater for providing a heat pulse thermally connected to the sample, and an adiabatic heat shield in which the sample holder is positioned and including an electrical heater. An electrical power supply device provides an electrical power output to the sample heater to generate a heat pulse. The electrical power from a power source to the heat shield heater is adjusted by a control device, if necessary, from one measurement to the next in response to a sample temperature-versus-time change determined before and after a previous heat pulse to provide a subsequent sample temperature-versus-time change that is substantially linear before and after the subsequent heat pulse. A temperature sensor is used and operable over a range of temperatures ranging from approximately 3K to 350K depending upon the refrigerant used. The sample optionally can be subjected to dc magnetic fields such as from 0 to 12 Tesla (0 to 120 kOe).

10 Claims, 15 Drawing Sheets

Microfiche Appendix Included
(1 Microfiche, 26 Pages)

CALORIMETRIC SYSTEM AND METHOD

CONTRACTUAL ORIGIN OF THE INVENTION

The United States Government has rights in this invention pursuant to Contract No. W-7405-ENG-82 between the U.S. Department of Energy and Iowa State University, Ames, Iowa, which contract grants to Iowa State University Research Foundation, Inc. the right to apply for this patent.

This application includes one microfiche Appendix B having a total number of twenty six (26) frames.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention relates to adiabatic calorimeter systems and methods.

BACKGROUND OF THE INVENTION

Many of the measurements of the properties of materials span temperature regions from cryogenic temperatures (e.g. 4.2K and below) to above 350–400K. In many cases, particularly for measurements such as heat capacity and any other calorimetry, a strict requirement is imposed on the quality of thermal insulation. That is, the best thermal insulation of the sample from the surrounding environment must be assured. Hereafter, the term "sample" is taken to mean a test material placed inside a sample holder with a temperature sensor attached to the sample holder.

In general, any type of measurement which requires a knowledge of the exact temperature difference between a certain initial state of the system before a temperature change process (e.g. a heat pulse) begins and the final state of the same system after a temperature change process is finished, ideally must be performed without energy (heat) losses or gains which occur due to the heat exchange with the surrounding calorimeter environment. Usually, these conditions are referred to as adiabatic. It is obvious that the ideal adiabatic conditions are not practically achievable. Therefore, the only way for the precise determination of the temperature difference between the initial and final states of the system is to design a system which will control, readjust, and maintain the temperature of the environment in accord with the current temperature of the sample. Typically, a high vacuum (e.g. $10^{-6}$ torr or better) provides an acceptable thermal insulation. However, it can not and does not eliminate all of the possible heat flows in a calorimetric system; e.g. heat exchange due to radiation effects, thermal conductivity of electrical wiring and/or sample support mechanisms, etc. All of the previously known apparatus and methods for automated or semiautomated temperature control of the environment and derived heat flow processes use an independent control circuit with a separate temperature sensor(s) directly (thermally) connected to the heat shield(s). The temperature of the surrounding environment is regulated by using one or more controlled temperature shields (i.e. adiabatic heat shields) with incorporated temperature sensor(s) and heater(s) based on the principle of maintaining the temperature of the environment (heat shield) as close as possible to the current temperature of the sample.

Alternately, a possible automated environment temperature control involves use of a commercially available devices (cryocontrollers) which can be programmed for certain temperature setpoints and which will maintain the temperature of the adiabatic heat shield(s) at or close to a selected setpoint. The setpoint typically is set at the sample's temperature or slightly below or slightly above it.

However, regardless of which technique is used for temperature of the environment (heat shield), separate independent temperature sensor(s) is/are necessary for the controlled temperature adiabatic heat shields and control devices are needed to control the heat flow process in the highly thermally insulated vacuum test chamber based on attempts to maintain the temperature of the environment approximately equal to the temperature of the sample.

Commercially available cryocontrollers are satisfactory in apparatus where heat exchange between the sample and the controlled adiabatic heat shields is relatively high. This situation typically is achieved by introducing a small amount of an exchange gas into the vacuum chamber (usually helium gas) to improve the thermal conductivity between all parts of the apparatus inside the vacuum chamber. Any cryocooler has a serious disadvantage from the standpoint that it initially overheats the apparatus (exceeds the setpoint). Then after the output power to the controlled heat shield heater is reduced, the temperature of the environment falls below the desired setpoint and continues to oscillate for some time. In high vacuum conditions, this behavior is unacceptable since it will take a relatively long time for the temperature of the adiabatic heat shield to fall once overheated. When the heat shield temperature finally falls, the temperature of the sample will change such that it will be necessary to readjust the cyrocooler's set point to another value. A similar disadvantage is to be expected using any calorimetric measurement method that is based on comparison of current temperature of the sample and the environment.

An object of the present invention is to provide a calorimetric apparatus and method operable without the need for direct determination of the temperature of the environment (i.e. without an adiabatic heat shield temperature sensor) and with the only sensor required being to measure temperature of the sample.

Another object of the invention is to provide a calorimetric apparatus and method where the calorimetric measurement is free of such unknown and variable environmental temperature effects as radiation, thermal conductivity of electrical wiring and sample support mechanism, etc.

Still another object of the invention is to provide a calorimetric apparatus and method in which electrical power to the adiabatic heat shield heater is adjusted, as necessary, in response to a measured sample temperature-versus-time behavior before and after a previous heat pulse to provide a subsequent sample temperature-versus-time change that is within preset control limits that simulate thermal equilibrium of the sample relative to the environment.

Still a further object of the present invention is to provide a calorimetric apparatus and method operable over a temperature range of approximately 3K to approximately 350K depending upon the refrigerant used and in optional dc magnetic fields up to 12 T.

SUMMARY OF THE INVENTION

The present invention provides apparatus and method for making a series of calorimetric measurements with respect to a sample disposed in a sample holder having a sample heater to provide a sample heat pulse. The sample holder is disposed within an adiabatic heat shield including an electrical heat shield heater. The sample temperature is measured before and after each pulse. From this measurement, a sample temperature-versus-time change is determined before and after each heat pulse. For each subsequent measurement, the electrical power output to the adiabatic shield electrical heater is controlled and adjusted, if necessary, in response to the previously measured sample temperature-versus-time change before and after a previous heat pulse to provide a subsequent sample temperature-versus-time change that is indicative of the sample being in a thermal equilibrium state relative to its environment. Control of the adiabatic heat shield heater power in response to prior in-situ sample temperature-versus-time behavior renders the calorimetric measurement free of such unknown and variable environmental temperature effects as radiation losses, thermal conductivity of electrical wiring and sample support mechanism, etc.

Apparatus in accordance with an embodiment of the invention for measuring heat capacity of a sample where a series of measurements are taken in succession comprises a sample holder in which a sample is disposed; a temperature sensor and a sample heater of which both are thermally coupled to the sample; and an adiabatic heat shield which includes an electrical heater and which surrounds the sample holder. Electrical power supply means provides the electrical power to the heat shield heater with the electrical power being adjusted by power adjusting means, if necessary, from one measurement to the next in response to the sample temperature-versus-time change determined before and after a previous heat pulse to provide a subsequent sample temperature-versus-time change that is indicative of the sample being in thermal equilibrium state relative to its environment; e.g. exhibiting a substantially linear temperature-versus-time change before and after the subsequent heat pulse and at a temperature change rate indicative of a sample thermal equilibrium state.

The electrical power supply means may comprise a dc current source under computer control to incrementally vary, if necessary, the power level of the electrical output to the heat shield heater from one measurement to the next in response to the prior sample temperature-versus-time change determined before and after a prior heat pulse as necessary to provide the subsequent sample temperature-versus-time change that is substantially linear before and after the subsequent heat pulse and at a temperature change rate indicative of a sample thermal equilibrium state.

The present invention thus in an embodiment controls and adjusts the electrical power output to the adiabatic heat shield heater within thermal equilibrium-simulating power control limits that provide measured sample temperature-versus-time changes that are independent of the aforementioned unknown and variable environment temperature effects.

For purposes of illustration and not limitation, for a series of heat capacity measurements, the rate of change of sample temperature before the temperature change process (foreperiod) must not be negative (must be zero or positive) and must be within a preset rate of change indicative of a sample thermal equilibrium state. The rate of change of sample temperature after the temperature change process (afterperiod) may be positive, zero, or negative and also must be within a preset rate of change which generally corresponds to the rate of change that occurred during the foreperiod. These control limits for the series of electrical pulses permit close proximation of thermal equilibrium conditions and allow the adiabatic heat shield electrical heater to be controlled independent of the actual difference between the sample temperature and the adiabatic heat shield temperature. Such control limits thereby permit calorimetric data to be measured at high accuracy.

Another embodiment of the present invention disposes the sample holder proximate a source of refrigerant that is thermally switched to the sample to provide sample temperatures ranging from approximately 3K to 350K depending upon the refrigerant used. The temperature sensor comprises a thin film resistor calibrated and operable over a range of temperatures from abut 3K to 350K to this end. Moreover, means can be provided to subject the sample to dc magnetic fields such as from 0 to 12 Tesla (0 to 120 kOe).

The aforementioned and other objects and advantages of the present invention will become more readily apparent from the following detailed description taken with the following drawings.

DETAILED DESCRIPTION OF THE INVENTION

Calorimeter Hardware Design

Figure 1:
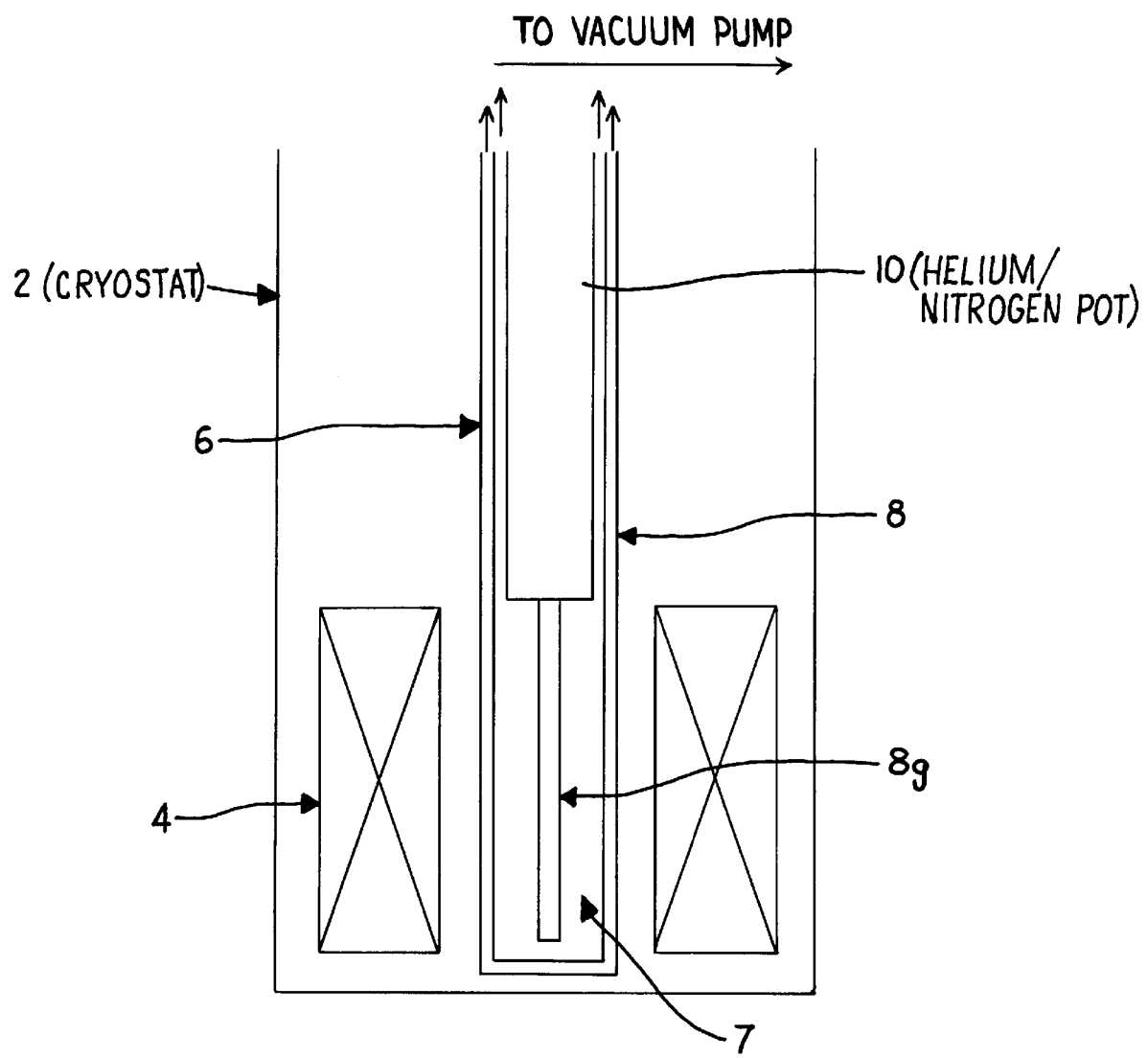
FIG. 1 is a schematic diagram of adiabatic calorimeter apparatus in accordance with an embodiment of the invention showing a cryostat and calorimeter insert loaded in the cryostat.
Figure 5A:
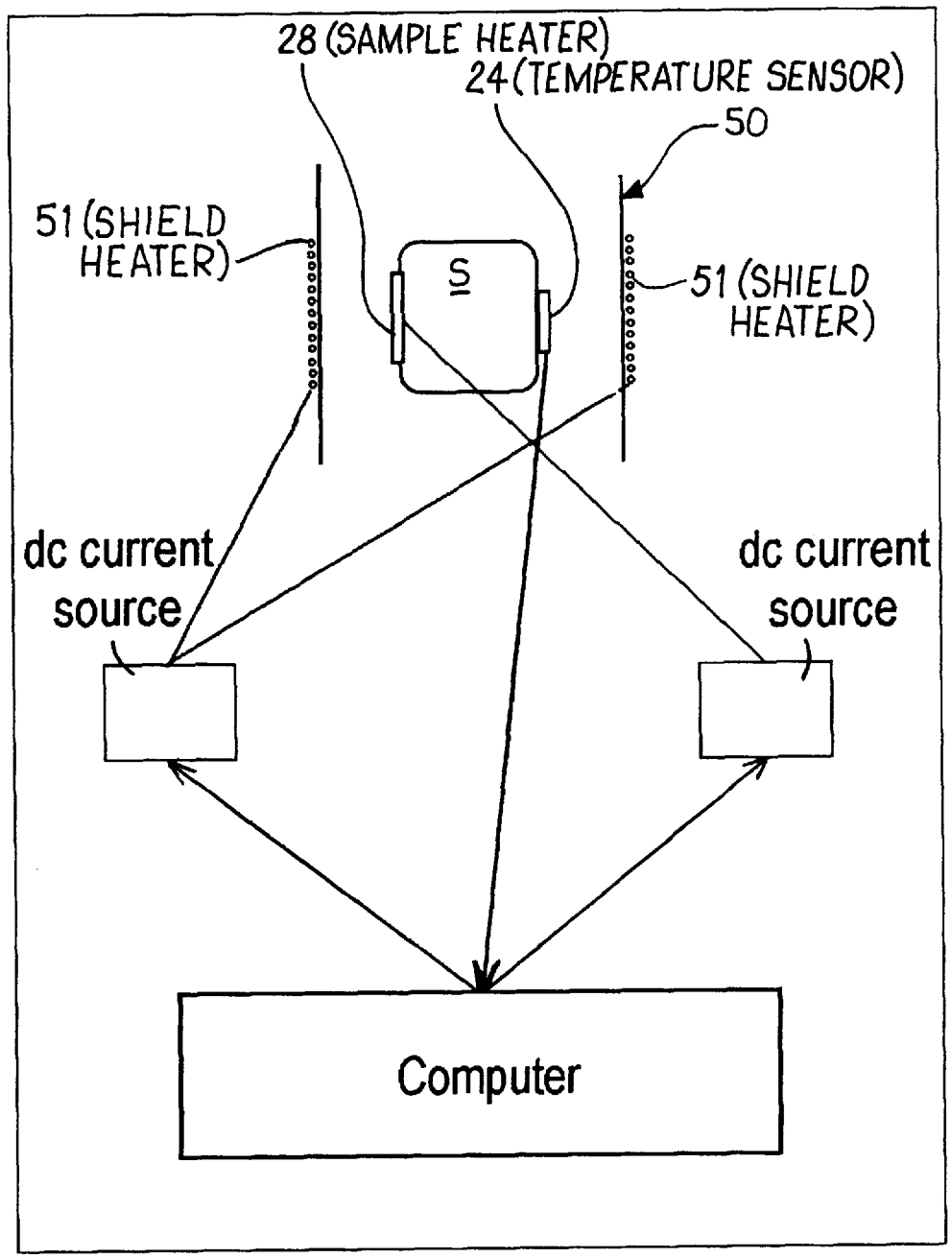
FIG. 5A is a schematic electrical block diagram showing a sample and adiabatic heat shield electrical resistance heater with associated dc current source, nanovoltmeter, digital multimeter/scanner, controller, and desktop computer.
Figure 5B:
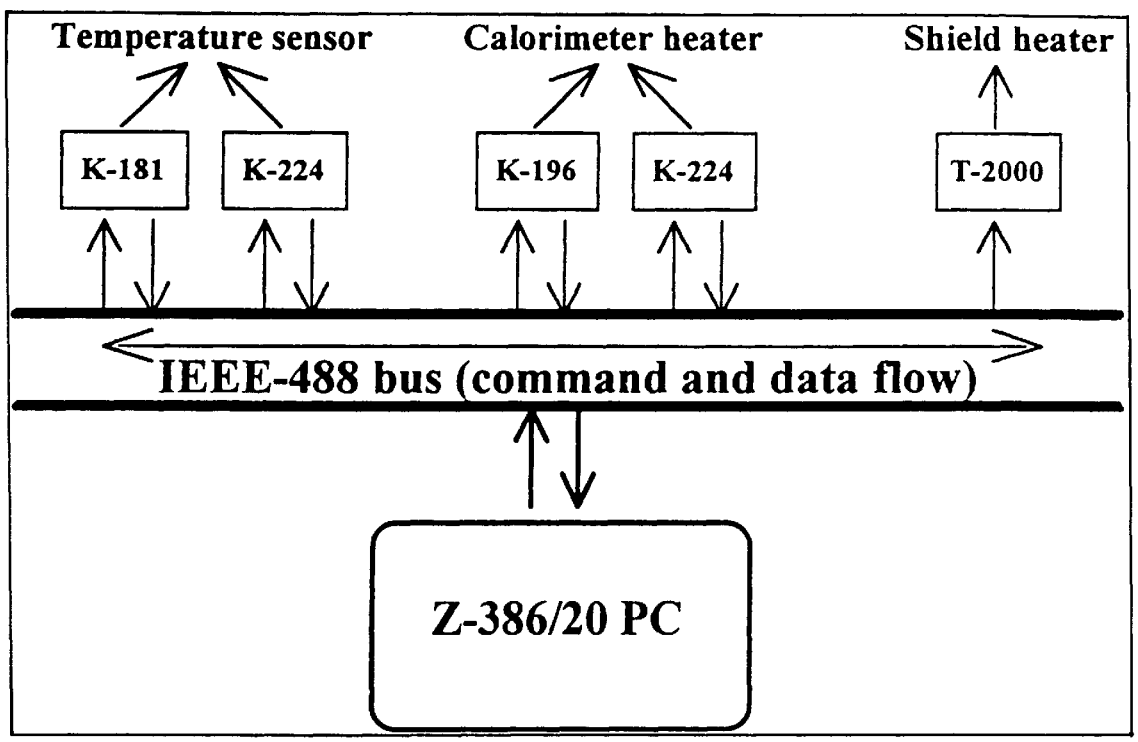
FIG. 5B is a schematic diagram showing all measuring devices and computer relative to a bus command/data line.

Referring to FIGS. 1–4, calorimetric hardware consists of the following major parts: a) cryostat 2 with a 12 Tesla superconducting magnet 4 (5 cm clear magnet coil bore with a 1 cm diameter×1 cm high homogeneous magnetic field)

manufactured by Cryogenic Consultants Ltd., London, England with a room temperature double layered vacuum insulated insert 6 which leaves approximately 2.5 cm clearance inside the magnet bore space; b) a calorimeter insert 8, FIGS. 1–2, which is received in the insulated insert 6 and which holds the calorimeter and a low temperature liquid helium/nitrogen pot 10 which allows cooling of the calorimeter to approximately 3K (separation between pot 10 and sample holder 12 (FIG. 3) described below is critical in reaching this low temperature, the shorter such a separation the better, such as 5.0 cm separation); c) current sources and voltage measuring devices shown in FIGS. 5A, 5B which include two Keithley model 224 dc current sources, a Keithley model 181 nanovoltmeter, a Keithley model 196 digital multimeter/scanner and a TRI Research model T-2000 cryocontroller (all devices are IEEE-488 compatible); 4) an IBM-PC compatible Zenith 386/20 desktop computer with National Instruments IEEE-488 GPIB board; 5) a high speed vacuum pumping system which attains a vacuum of $10^{-7}$ Torr.

Figure 2A:
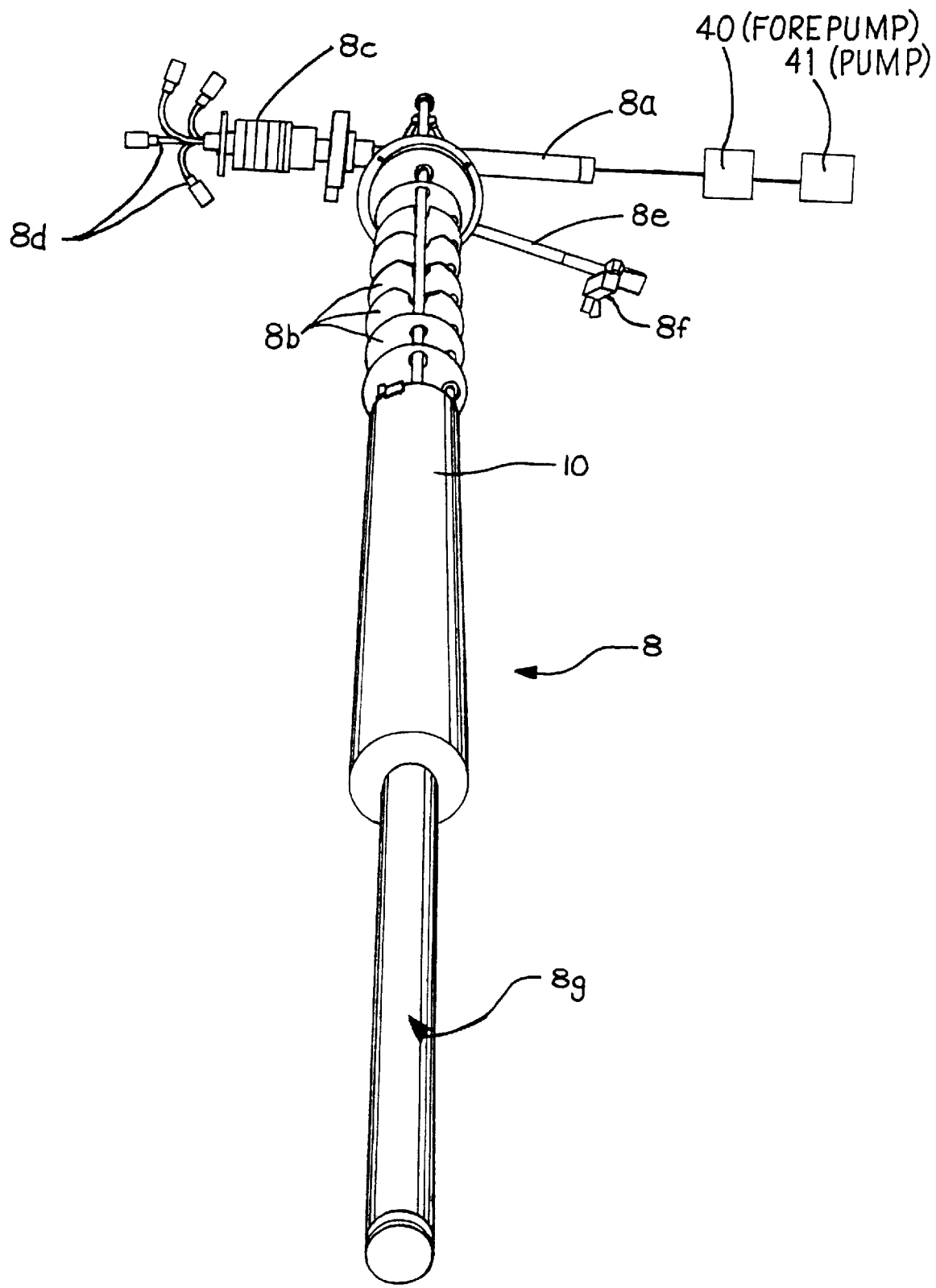
FIG. 2A is an enlarged view of the insert.
Figure 2B:
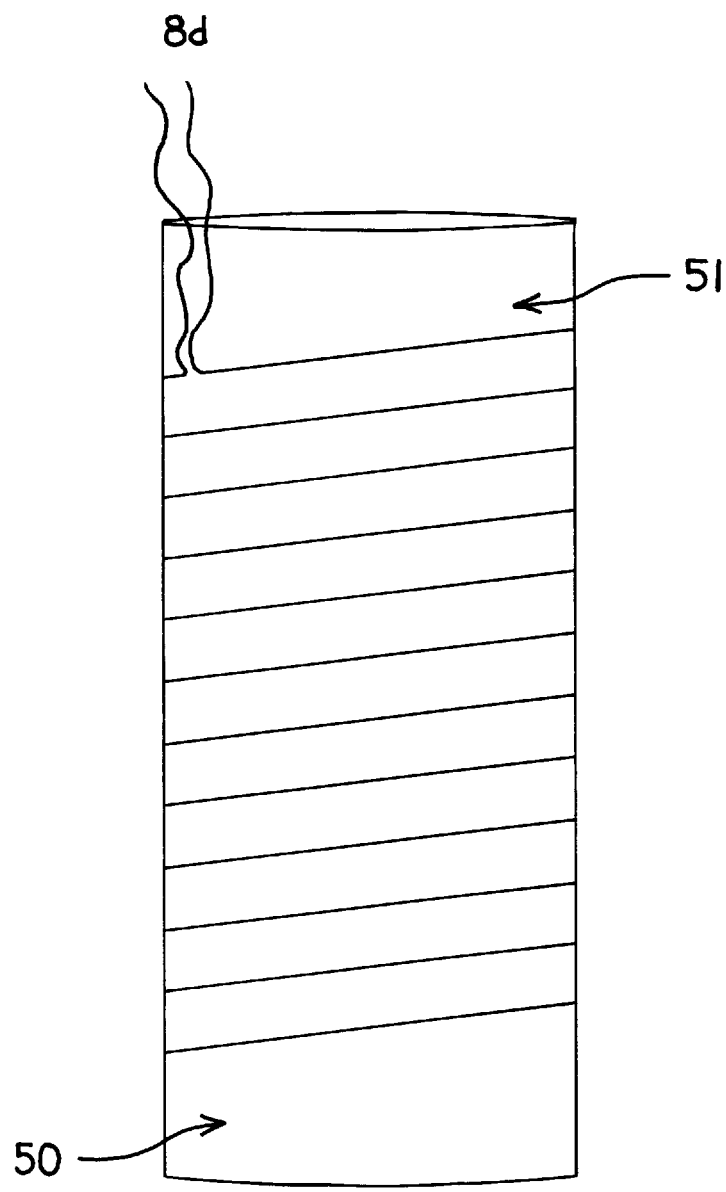
FIG. 2B is an enlarged view of the adiabatic heat shield with the electrical resistance heater wire wound around the shield.

The insert 8, FIG. 2A, includes a high vacuum conduit or line 8a, a plurality of heat dissipating baffles 8b, and a vacuum-tight, feed-through 8c for electrical connector wires 8d to the electrical components as shown in FIGS. 5A, 5B. The insert 8 also includes a helium/nitrogen exhaust and helium pumping conduit 8e having a valve 8f with the conduit 8e communicated to the pot 10 and to a helium pumping system which permits one to lower the temperature of the liquid helium inside the helium pot 10 from about 4.2K to about 1.5 to 1.7K. A copper heat shield assembly 8g is disposed about the sample holder 12, FIG. 3. FIG. 2B shows in detail the controlled portion of the adiabatic heat shield. It consists of a hollow copper cylinder 50, which fits tightly around the sample mounting frame 34 (FIG. 4) with a 15 Ohm electrical resistance heater wire wound around it. The shield heater is connected to the power source via electrical wiring 8d. The sample holder is located inside this controlled power heat shield and the latter is located inside the outer, non-controlled portion of the heat shield 8g, FIG. 2C.

Figure 2C:
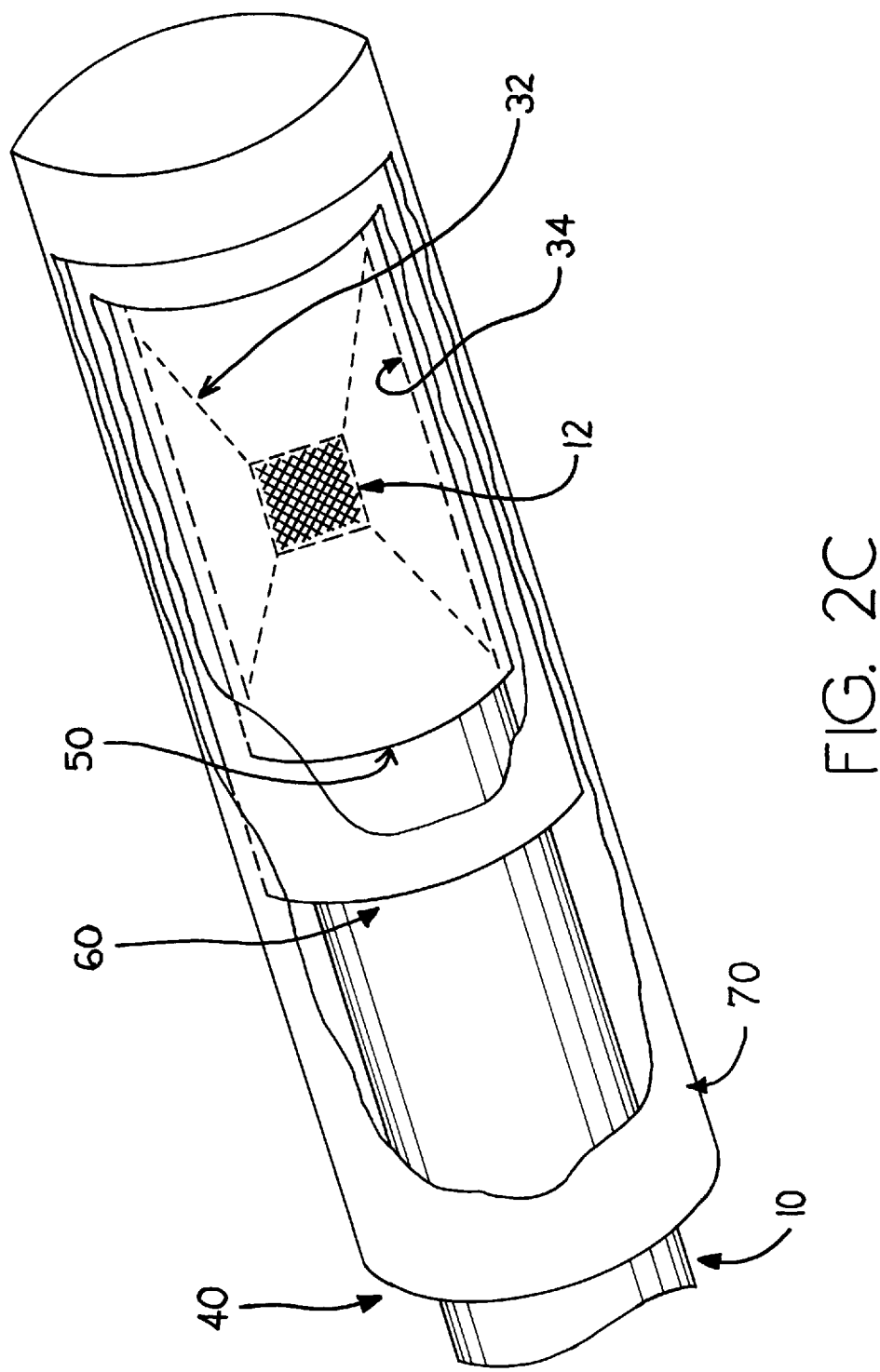
FIG. 2C is an enlarged view of the outer and middle radiation shields and the adiabatic heat shield, FIG. 2B, relative to the bottom of the helium pot, the sample mounting frame, and the sample/sample holder system.

FIG. 2C shows the shield assembly as comprising three hollow copper cylinders: the outer shield 70, the middle shield 60, and the inner adiabatic shield 50 which was just described (FIG. 2B). The middle shield 60, the outer shield 70 and the inner shield 50 form a series of three concentric cylinders which form the nearest sample surroundings. As described above, only the inner shield 50 has an active heater thermally connected to it (i.e. wound around it). The temperature of the middle and the outer shields floats and depends on the output power supplied to the inner shield heater, on the quality of the insulating vacuum, and on the conditions (temperature) outside the outer shield.

Figure 3A:
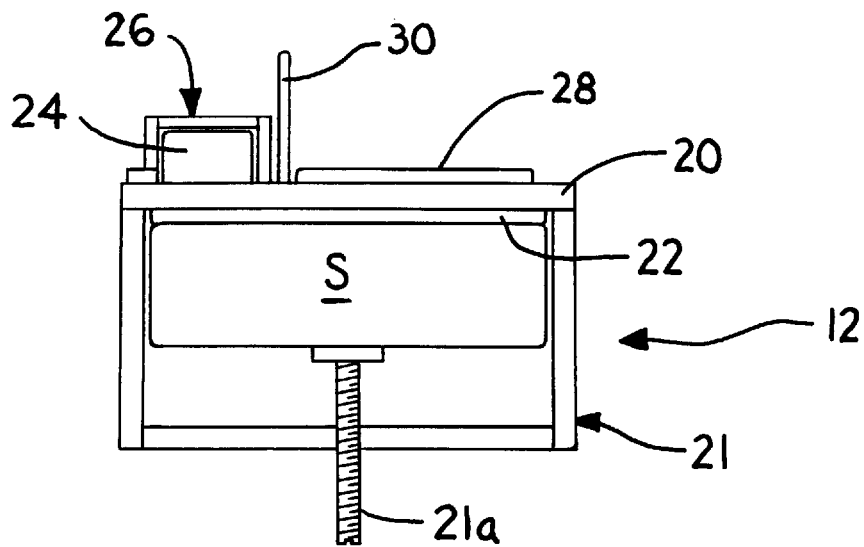
FIGS. 3A, 3B are enlarged schematic views of the sample holder.
Figure 3B:
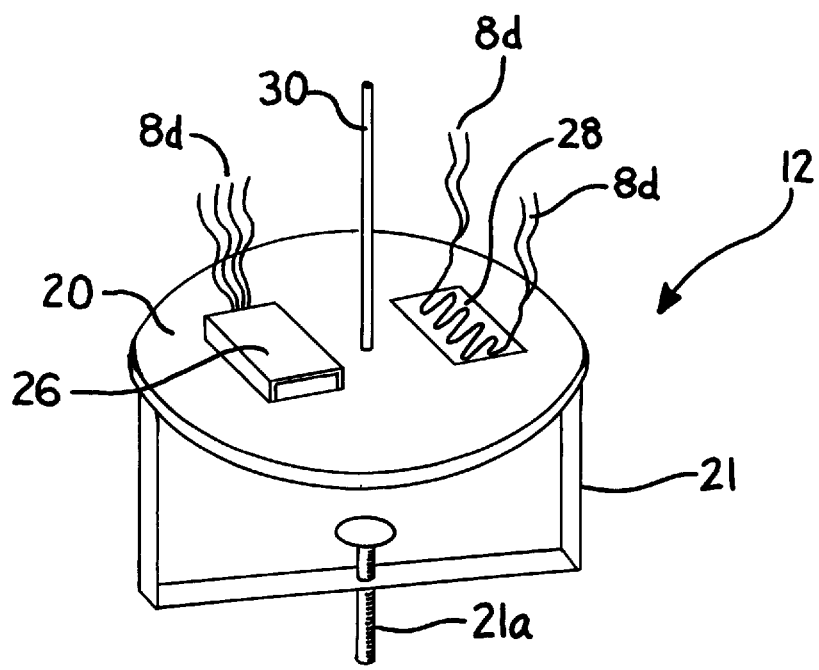
Figure 4:
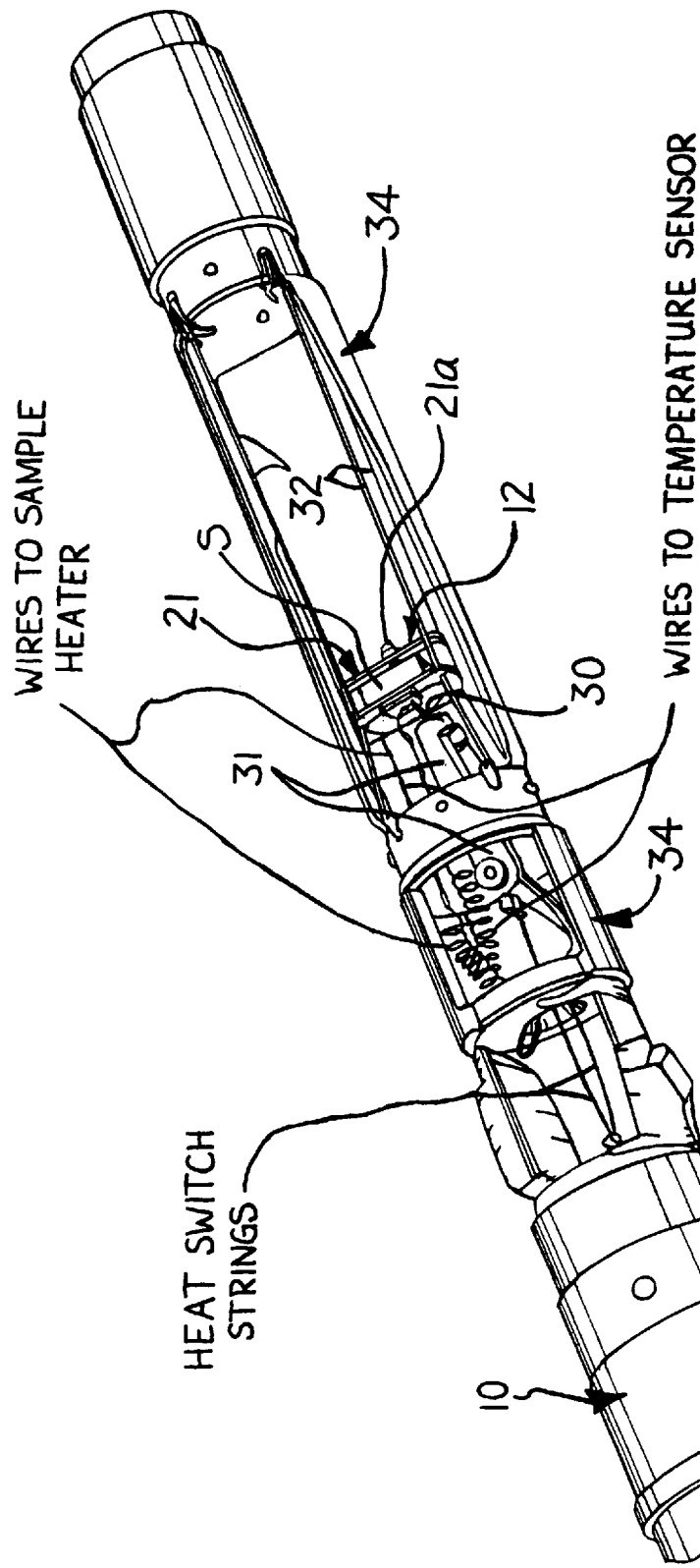
FIG. 4 is a perspective view of the sample holder shown proximate the bottom of the helium pot of the calorimeter insert.

Referring to FIGS. 3A, 3B and 4, the sample holder 12 is made from a low-oxygen pure copper (99.99+wt. % Cu) because a high thermal conductivity is necessary for a calorimeter capable to cover a wide range of temperatures from below 4.2 to 350K.

The sample holder 12 is shown schematically in FIG. 3A and in perspective in FIG. 3B. It is a clamp-like sample holder, where the sample S is held tightly to the main round copper plate 20 by pressure developed from the copper screw 21a disposed on copper frame 21. A measured amount of 50:50 (by volume) mixture of Apiezon-N grease and fine silver powder 22 is placed between sample S and main holder plate 20 to improve the thermal connection. All copper parts of sample holder 12 are soft soldered together. A CERNOX thin film resistor temperature sensor 24 is inserted in a tightly fitted copper clamp 26 and is held in place by using GE 7031 varnish, which also improves the thermal contact. A thin film strain gage CEA-06-062UW-350 from Measurements Group, Inc. comprises a sample heater 28 (i.e. the strain gage has a resistance of 350 Ohms and is used as a resistance heater) and is mounted on the same side of copper plate 20 as the thermometer 24 using a silver epoxy. The sample heater 28 provides a heat pulse to the sample S via the plate 20. The sample heater power supply comprises a Keithley model 224 dc current source. The use of the silver epoxy was dictated by the fact, that upon thermal cycling between room temperature and 4.2K, the GE 7031 varnish in time develops microcraks, leading to an unsatisfactory thermal connection of the sample heater 28 and sample holder 12. Cooling of the sample holder 12 and sample S is provided by means of mechanical heat switch 30 comprising a short copper wire connected to and disconnected from a modified alligator clamp 31, which is permanently thermally shortened to the low temperature helium pot 10 located above sample holder. The heat switch is connected to the alligator clamp 31, when its two jaws are closed (i.e. the heat switch wire is squeezed between the two jaws of the clamp), and is disconnected from the clamp 31 when its jaws are opened (spaced apart). The clamp 31 is operated by metal strings, FIG. 4, which extend out of the insert and cryostat for manual actuation to open and close the clamp jaws. The sample holder 12 is permanently hung by means of four thin (0.15 mm) nylon threads 32, FIGS. 2C and 4, to a massive copper frame 34. The frame 34 is permanently attached to the bottom of a low temperature helium pot 10. The low temperature helium pot 10 together with the massive copper frame 34 and including the hung sample holder 12 form the removable part, FIG. 2A, of the calorimetric system which fits inside the room temperature vacuum jacketed insert 6 inside the cryostat 2. The thermal insulation of the calorimeter with the mechanical heat switch 30 opened is ensured by pumping the insert space 7 (FIG. 1) where the calorimeter 8 is located down to a vacuum level of $1 \times 10^{-7}$ Torr. The pumping system comprises a high capacity mechanical forepump 40 providing vacuum of an order of $10^{-3}$ Torr) and a high capacity diffusion pump 41 (providing vacuum of an order of $10^{-7}$ Torr) connected to conduit 8a.

The copper heat shield assembly 8g comprises a set of heat shields which surround the massive copper frame 34 that holds the calorimeter. The set of heat shields consists of three cylindrical copper shields. An inner shield 50, FIGS. 2B and 5A, which is actually an adiabatic heat shield meaning that the temperature is being adjusted by means of regulating electrical power output, has a 15 Ohm electrical resistance heater 51 wound around its outer surface. Two spaced apart outer shields are simple radiation shields, and their temperatures drift depending on the inner shield heater output. More details on how the temperature of the inner adiabatic heat shield 50 is controlled are given in the next section.

Data Collection Software and Adiabatic Heat Shield Control

In one embodiment, the invention provides a completely automatic calorimetric system, where all data collection procedures are fully automated and are computer controlled. FIGS. 5A and 5B show a schematic diagram of how all system components are connected together with a personal computer. The system uses the conventional IEEE-488 general interface which ensures fast and reliable command, and data transfer from the computer and back from measuring devices.

The main part of data collecting software is comprised of FORTRAN subroutines complied using Microsoft FORTRAN-5.10 compiler. All procedures, responsible for command and data interchange between the computer, IEEE-488 board and measuring devices are written in C language and compiled using Microsoft Visual C/C++–8.00 compiler. Both FORTRAN- and C-based codes are linked together into a single executable module, which supports the following: a simple calorimeter temperature monitor which reads the resistance of a thin film resistor (sensor 24), editing several data collecting parameters and the actual process of collecting data over a specified temperature interval. The data collecting software has been designed to ensure that no measured heat capacity data are lost in the case of accidental power failure. The software output is organized into two output data files. The first one contains actual results of heat capacity measurements in a form of list of the median temperatures, specific heats (molar heat capacity of the sample, and the total and sample holder heat capacities), with their calculated standard uncertainties, and the data collection time. The second output file contains all the raw data, including sample heater current and voltage, inner heat shield output, and the actual temperature-time tables for every data point taken, so that this file may be reprocessed at later date for re-valuation of the heat capacity if the need arises. Simultaneously, with file directed output, all collected data are displayed in two windows in a form of two graphs: one is the plot of heat capacity versus temperature for all data points collected up to the moment, and the second is a temperature-time diagram for the data point currently being measured. Such an instantaneous real time visualization permits a quick check of whether or not everything is going well with data collection by means of just a brief look at the computer monitor screen.

A sensorless algorithm to control the inner adiabatic shield temperature, which is done automatically by data collecting software rather than by the cryocontroller's microprocessor or computer. The algorithm is based on a constant monitoring of the calorimeter temperature behavior versus time before and after the heat pulse (i.e. without an energy input from the sample heater). Since the heat flow between the sample holder, the adiabatic heat shield, and the surroundings inside the vacuum chamber is governed by Newton's law of cooling, then the behavior of the temperature of the sample should be one of the following:

1. Sample temperature does not change. This occur only when sample temperature is exactly equal to the temperature of the environment. It is the most rare case, however this state once achieved can exist indefinitely long.
2. Sample temperature slowly rises. Obviously this happens when sample temperature is lower than that of the environment.
3. Sample temperature slowly decreases. It occurs when sample has a higher than the environment temperature.

Thus, after a single measurement is completed (i.e. one knows the sample's equilibrium temperature versus time behavior during the foreperiod and a similar equilibrium temperature versus time behavior for the afterperiod) all of the information, which is necessary to make a decision of how to affect the power output to the adiabatic shield heater 51 is known without using a separate adiabatic shield temperature sensor. The problem of the environment temperature control therefore can be solved solely on the basis of sample's temperature behavior rather than on the basis of a comparison of the actual temperature of the sample and the environment. The requirement to make environment temperature control automatic implies that certain limits need to be established for rate of sample's temperature change during foreperiod and during afterperiod. The following limiting conditions were selected: Foreperiod—the rate of temperature change may not be negative; and it is desirable that it does not exceed 0.03K/min; Afterperiod—the rate of temperature change should not exceed 0.03K/min. The basic shield heater 51 manipulations, therefore, become as follows: 1) when the sample's temperature in the afterperiod rises more than 0.03K/min, then the software reduces the shield heater power and proceeds with measurements of the next data point; 2) when the sample's temperature in the afterperiod rises less than 0.03K/min, then the software does not affect the shield heater power and proceeds with measurements of the next data point; 3) when the sample's temperature in the afterperiod is decreasing, this means that for the following foreperiod it would have the same sign too, then the software increases the power of shield heater 51 and monitors sample temperature change for half of the time usually required to accomplish the measurements in foreperiod or afterperiod. This operation is repeated until temperature change becomes positive during this "waiting" time, and then the software proceeds with measurements of the next data point. The algorithm is described in detail in the Appendix A set forth below. Software embodying the algorithm is set forth in microfiche Appendix B.

The power supply for the adiabatic heat shield heater 51 is a TRI Research cryocontroller, model T-200, which is rated at 50 W full power. All power output adjustments are made at small increments equal to 0.1% of rated power, i.e. at 0.05 W (50 mW) steps. This was found to be sufficiently quick and accurate way to control the temperature of the surroundings.

EXAMPLE 1

After a single measurement was completed, a least squares fit of the temperature versus time dependence during the afterperiod showed that sample temperature changes at a rate 0.016K/sec. The corresponding foreperiod temperature change rate was 0.017K/sec. Since the afterperiod rate is lower than that of the foreperiod and they both fall within the established limits, then no adiabatic shield heater power adjustment is necessary. The data collecting system proceeds with next measurement starting with another foreperiod.

EXAMPLE 2

After a single measurement was completed, a least squares fit of the temperature versus time dependence in the afterperiod showed that the sample temperature changes at a rate –0.005K/sec. Since the measurements were made in the afterperiod, then the following foreperiod measurements will most likely show a similar (negative slope) behavior. Since it does not comply with established criteria, that temperature change during the foreperiod may not be negative, a shield heater power increase is necessary. The control system increases power to heater 51 by 0.1% and then monitors sample temperature behavior for a period of time equal to ½ (50%) of a typical foreperiod and afterperiod measurement (i.e. 20 seconds). If temperature change rate stays negative, another 0.1% increase of heater power is made and so on until it becomes non-negative. Then data collecting system proceeds with a complete single measurement.

EXAMPLE 3

After a single measurement was completed, a least squares fit of the temperature versus time dependence in the afterperiod showed, that sample temperature changes at a rate 0.016K/sec. the corresponding foreperiod temperature change rate was 0.007K/sec. Since calorimetric data are taken on warming (i.e. sample's temperature rises), and under normal conditions the temperature of the adiabatic heat shield 50 stays practically unchanged, then this situation detects a specific system condition, which is when the liquid helium (which is normally used as a refrigerant to cool system and sample down to the lowest achievable temperature) is exhausted and environment temperature begin to rise spontaneously. Therefore the system shuts down the adiabatic shield heater 51 and proceeds with foreperiod measurements to collect a next single data point.

EXAMPLE 4

After a single measurement was completed, a least squares fit of the temperature versus time dependence in afterperiod showed, that sample temperature changes at a rate 0.033K/sec. This value exceeds the established limits. Therefore the control system reduces adiabatic shield heater power by 0.1%. In the special case when the adiabatic shield heater 51 is inactive (see example 3, above), no adjustment is made and shield heater remains inactive. The data collecting system proceeds with the next single measurement.

Figure 6:
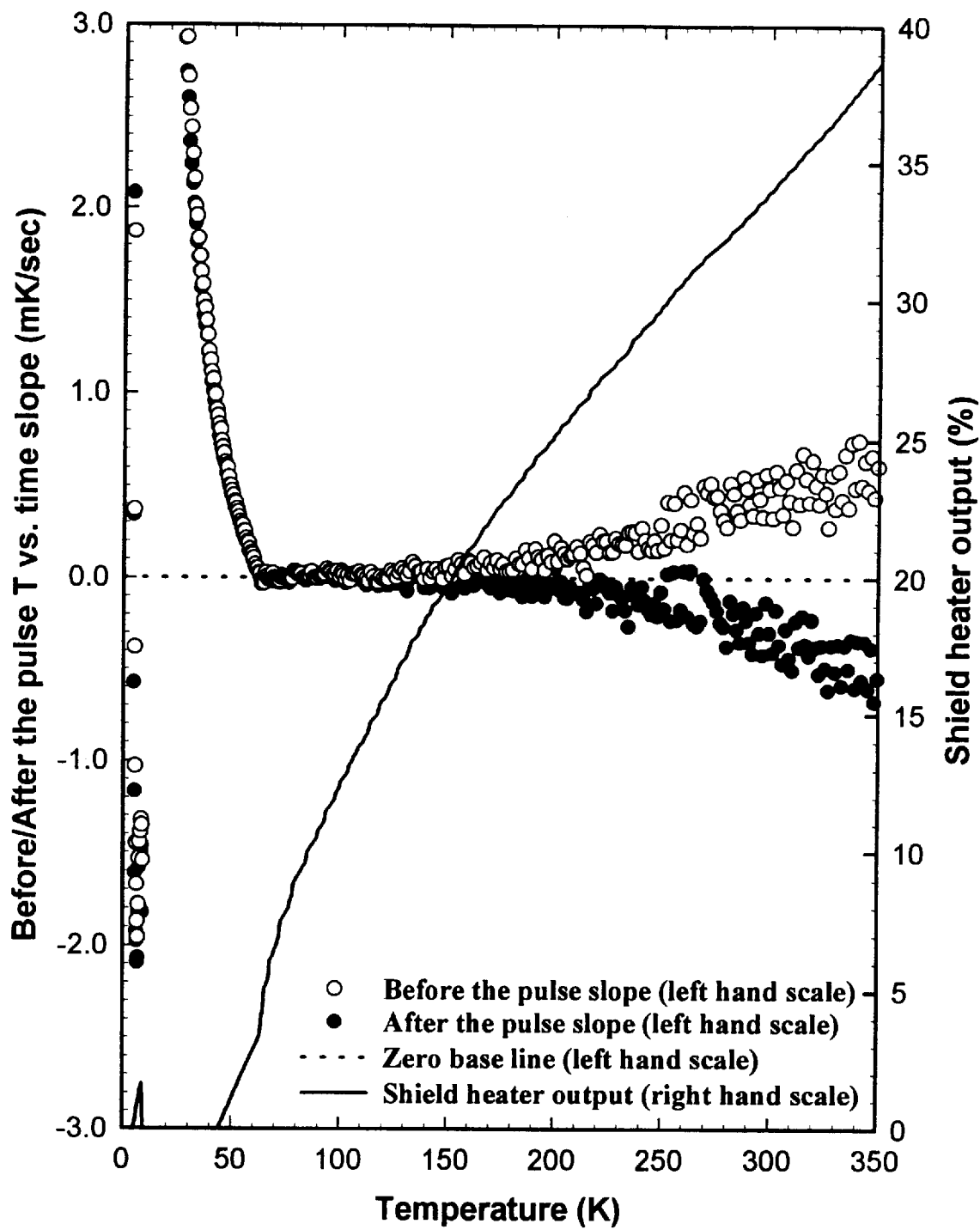
FIG. 6 is a graph of before- and after-pulse temperature versus time slopes and adiabatic shield heater output for a copper standard weighing 1.6217 grams calibration run.

The practical results, presenting the sample's temperature behavior (i.e. the heat exchange process between the sample S and the environment) over the temperature region from 3.5K to 350K during the heat capacity measurements of pure copper is shown in FIG. 6. The curve, which represents the percent of adiabatic shield heater (51) power is shown in the same graph. It is obvious, that the liquid helium (refrigerant) loss occurred approximately at 10K, and because of a spontaneous and sharp environment temperature rise, the control system automatically deactivates the adiabatic shield heater 51. The adiabatic shield heater 51 again becomes operational approximately at 45K. And starting from 55K the adiabatic shield control without using a separate temperature sensor becomes very accurate, i.e. a sample's temperature change slope is small and positive for every foreperiod, and has approximately the same magnitude, but negative in afterperiods, indicating, that adiabatic heat shield 50 was maintained at almost ideal conditions: approximately at median sample temperature. Such an excellent control ensures, that the calorimetric data can be taken at a highest possible accuracy. The important point here is that there is no preset profile for the shield heater power output, i.e. it is governed only by the current state of the heat transfer between the surroundings and the calorimeter. The usage of a small shield heater power increments (50 mW steps) eliminates the need for long wait periods for a shield temperature stabilization, and what is more important, it completely eliminates any short time heat shield temperature fluctuations which cannot be avoided using an internal cryocontroller's microprocessor.

Heat Capacity of Copper Standard and Calibration Results

No calorimeter can be used without a precise calibration; i.e. without determining the raw heat capacity of a sample holder and related components such as heater, temperature sensor, grease, etc. and then checking out the calibration result against a well established heat capacity standard. It has been accepted that high purity copper is the best calorimetric standard for temperature regions mentioned above since its heat capacity is considered to be well established within an accuracy better than 0.5%.

Figure 7:
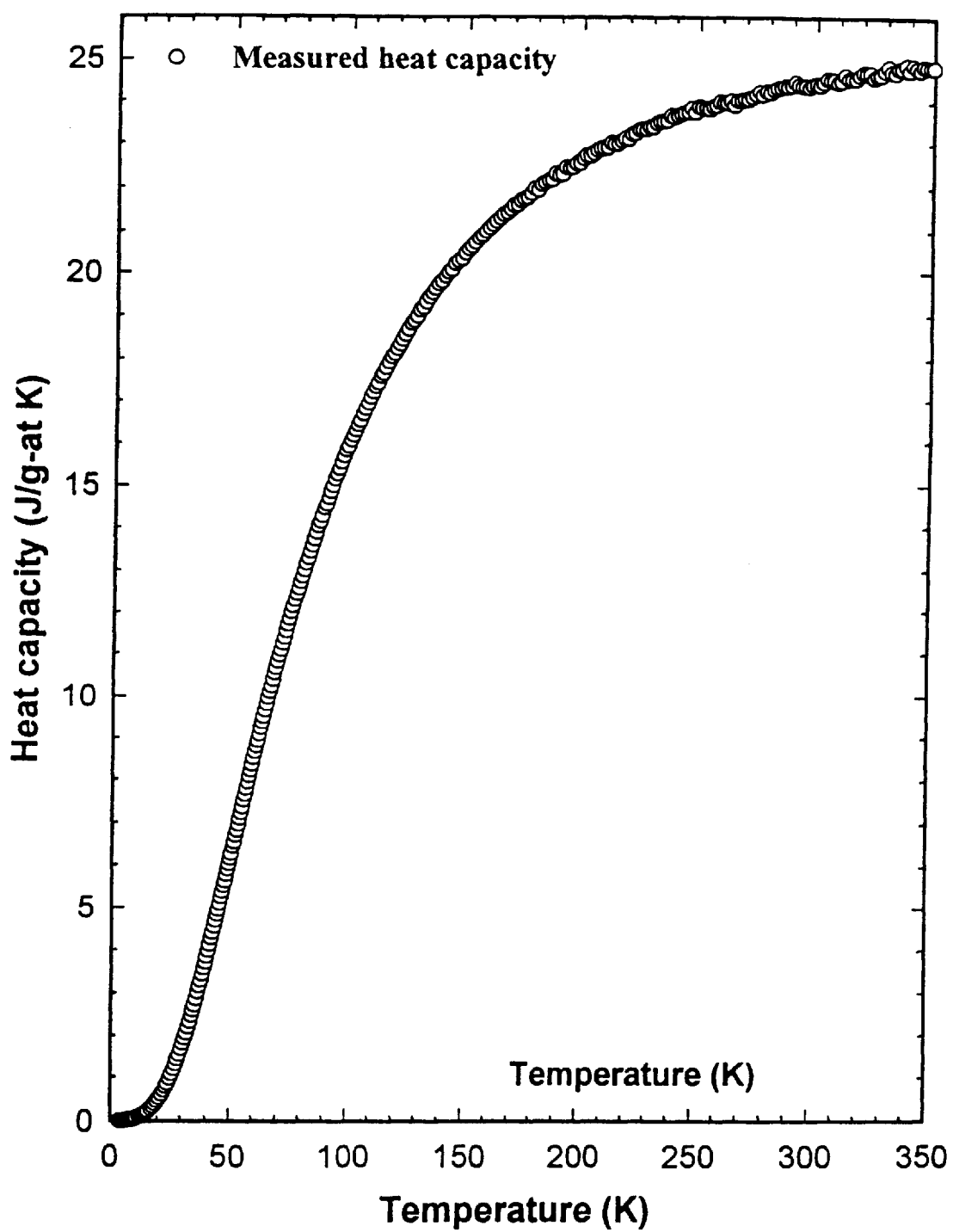
FIG. 7 is a graph of heat capacity of a copper standard weighing 1.6217 grams from 3.2 to 350K.
Figure 7A:
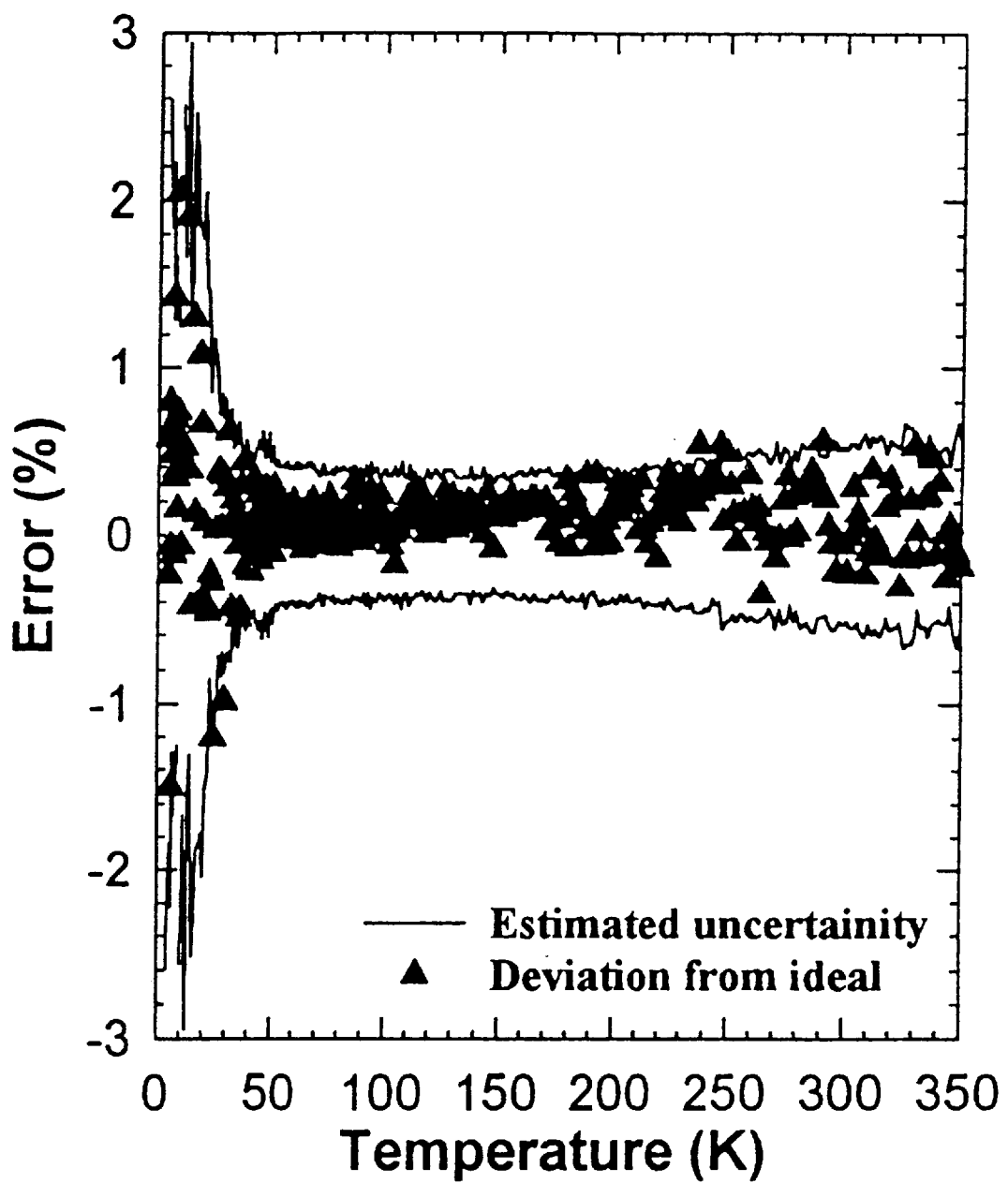
FIG. 7A is an inset in FIG. 7 and represents estimated uncertainties (the area delineated with the solid lines) together with deviations of observed data from a recommended values (filled triangles) in percent.

Three independent calibration runs were made using the apparatus described above to ensure that heat capacity of the empty sample holder and related components was determined with high precision over the whole temperature region (approximately 3K to 351K). A total of approximately 750 data points were combined to represent an empty calorimeter raw data heat capacity data, which are substracted from the measured total heat capacity (sample+ sample holder+related components) during future experiments. The heat capacity of the empty calorimeter varied from approximately 0.1 mJ/K at 3K to 650 mJ/K at 350K. To ensure that the calibration had been done corectly, the heat capacity of 1.6217 grams calorimetry conference copper standard was measured. The results are shown in FIG. 7 in the form of a plot of molar heat capacity and in the inset, FIG. 7A, the deviations of the observed data from the recommended values for the heat capacity of pure copper together with estimated uncertainties of measurements.

The heat capacity of the copper standard was measured using sample heater heat pulses in which the temperature rise delta T was equal to 1% of the temperature at which the measurement was being made and with the additional restriction that delta T was greater than 0.5K and less than 1.5K. The inset, FIG. 7A, clearly shows that the calorimeter of the invention gives very reliable results, showing no significant systematic deviations form the accepted copper heat capacity values. The random deviations (filled triangles) range from approxiamtely 0.5% to 0.7% between 25K and 350K. Below about 25K, there are several data points which deviate from the recommended values as much as plus or minus 1% to 2% due to the temperature rise of the surroundings in this temperature range being spontaneous and significant (FIG. 7) such that the semiadiabatic conditions are not strictly met.

Another important feature from the aforementioned test data is that the estimated standard uncertainties (the solid lines in FIG. 7A) give completely realistic numbers, since almost all of the observed delta C values (uncertainty values) fall inside the area delineated by the plus or minus σC curves, where delta $C=(C_{observed}-C_{recommended})/C_{observed} \times 100$ (%), and σC is the evaluated uncertainty in %. Therefore, these calculated uncertainties can be safely used in calculations for evalution of the uncertainites of all of the derivative physical and thermodynamic parameters based on the experimental heat capacity data.

Appendix A

Heat capacity measurements basics

It is well known, that heat capacity (C) is a thermodynamic function which represents the material's response to introduced amount of energy (Q) through change of the temperature (T) and is defined as:

$$C = \frac{\partial Q}{\partial T} \quad (1)$$

In practice, heat capacity measurements utilizing Nernst method, are based on Eq.1 in the following way: after applying a known amount of heat (ΔQ) to the specimen and measuring the corresponding temperature change (ΔT), the heat capacity at median temperature ($T_m$) is given as:

$$C = \frac{\Delta Q}{\Delta T} \quad (2)$$

The extreme simplicity of Eqs. 1 and 2, unfortunately does not directly transform into a simplicity of heat capacity measuring hardware and software. First of all, it follows from Eq.1, that heat capacity should be measured with a small amounts of added energy, ΔQ, so that ΔT (Eq.2) is as small as possible. In practice, however, a lower limit for ΔQ is such, that the resulting ΔT varies from approximately 0.05–0.5K at 4.2K to approximately 1–10K at ~300K, mainly due to the limited accuracy and resolution of available temperature sensors. Another important behavior, which complicates practical measurements, is shown in the FIG. 8, where the idealized time-temperature behavior is shown together with the real one. Idealized conditions for adiabatic heat capacity measurements can be described as follows: i) the sample temperature is constant at least for a certain period of time immediately before and instantly after the heat pulse, ii) the heat pulse has been applied to a sample instantly (over infinitely short period of time), and iii) the sample responds to a heat pulse by rising its temperature immediately, i.e. assuming that the sample's thermal conductivity is unlimited (or is infinitely high) These ideal conditions are shown as solid lines in FIG. 8. As for this case the experimental procedure of heat capacity measurement would be very simple and requires only a knowledge of sample's temperature before the heat pulse (i.e. what was the sample's temperature $T_1$ at the moment of time $t_1$ just before the heat pulse), the amount of energy (ΔQ) given instantly to a sample at $t_1$, and what is a resulting temperature $T_2$ at the same moment of time $t_1$ after the instant temperature rise due to the pulse. It is obvious, that the temperature rise (ΔT) is given as:

$$\Delta T = T_2 - T_1 \qquad (3)$$

and median temperature, $T_m$ (i.e. temperature for which heat capacity has been measured) is determined as:

$$T_m = \frac{T_1 + T_2}{2} \qquad (4)$$

Adiabatic (ideal) and semiadiabatic (real) conditions

Figure 8:
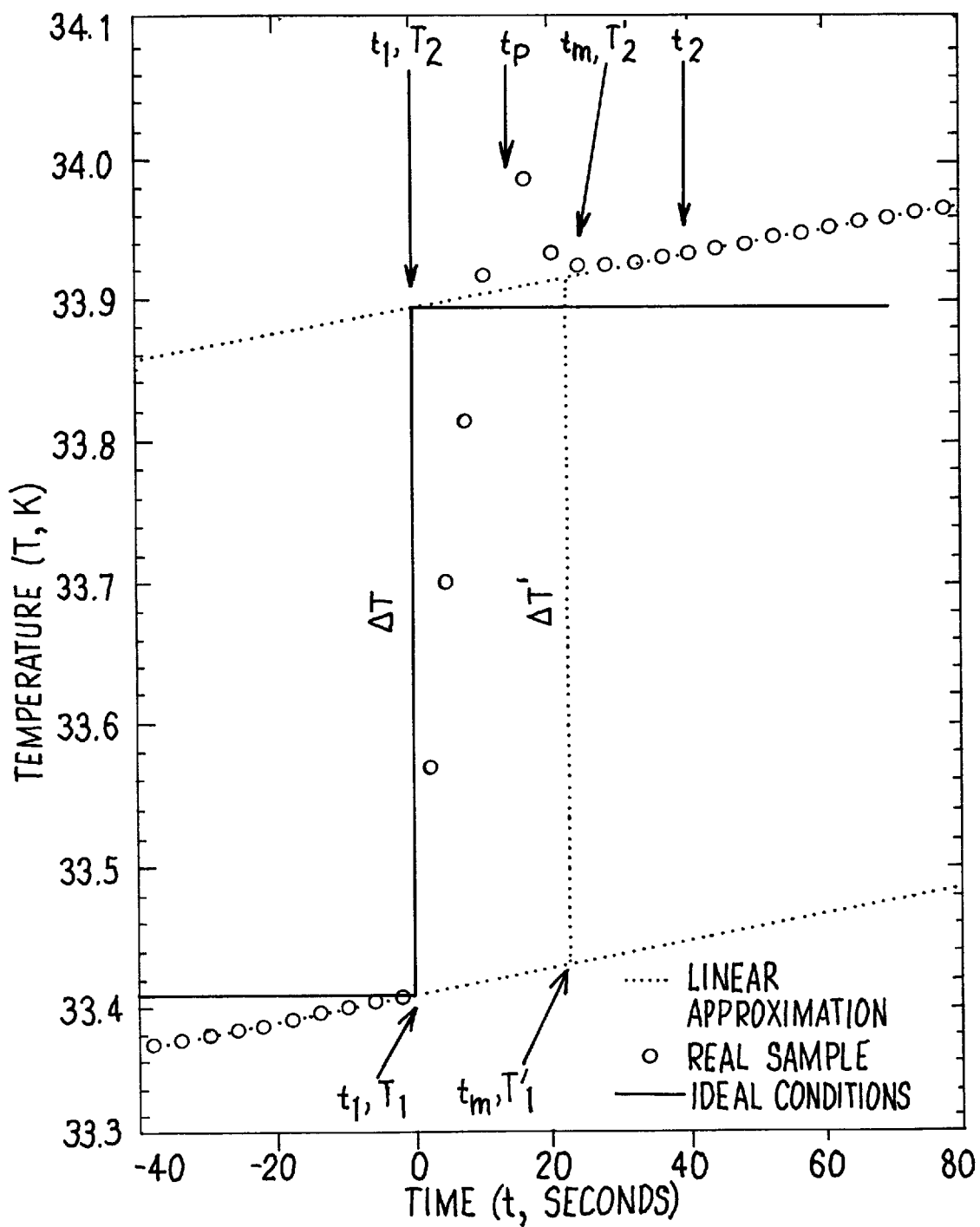
FIGS. 8 and 9 are time-temperature heat-pulse diagrams.

The ideal conditions mentioned above, however, can not be achieved. First of all it is impossible to design a calorimeter with a perfect insulation from the surroundings, i.e. it is impossible to eliminate all heat leaks to or from the sample. Second, it is impossible to produce an instantaneous heat pulse—it always requires a finite amount of time, which can not be assumed to be negligibly small. And third, there is no solid which conducts heat instantly, therefore an even distribution of the added energy throughout the sample always require a certain time. A typical real sample behavior is shown in FIG. 8 as open circles in a temperature (T) versus time (t) plot. Therefore, the only practical way for accurate experimental measurements to be performed is to create conditions as close to ideal as possible. This means at least the following:

The sample must be thermally insulated from the surroundings as well as possible, and the temperature of the surroundings should be kept as close to the sample's temperature as possible to minimize any positive and negative heat leaks. Such conditions are typically considered as semiadiabatic, and usually when the temperature difference between sample and surrounding is small, the sample's temperature changes linearly (see the following section) during given period of time.

The heat should be added to the sample as quickly as reasonably possible;

The calorimeter design should ensure that sample/sample holder assembly after the heat pulse comes to internal thermal equilibrium as well as to thermal equilibrium with the surroundings as soon as possible.

The open circles in FIG. 8 show, that sample's temperature is rising slowly and linearly before the heat pulse (time $t_1$) due to a small positive heat leak from the surroundings.

The heat pulse, which begins at $t_1$ causes a sharp increase of a sample's temperature until the time $t_p$, when the heat pulse has been canceled. It takes a certain time (from $t_p$ until $t_2$, which usually is referred to as the internal thermal relaxation time, or simply the relaxation period) for the energy to be distributed evenly through the sample/sample holder assembly. After time $t_2$ the temperature again shows a linear behavior with time. Therefore, the determination of the real temperature rise ΔT', which replaces the ideal ΔT, has to be done through a least squares linear approximation of the temperature versus time behavior before the heat pulse ($t_1$) and after the heat pulse (starting at $t_2$) using the following extrapolation of the before and after heat pulse linear regions to a median time $t_m$, where $$t_m = \frac{t_1 + t_2}{2} \qquad (5)$$

to estimate the idealized (before the pulse temperature) $T'_1$ and after the pulse temperature $T'_2$ at $t_m$. The values of ΔT and $T_m$, which are necessary for the evaluation of the heat capacity are determined by substituting $T_1$ and $T_2$ by $T'_1$ and $T'_2$, respectively, in Eqs. 3 and 4.

Establishing the existence of semiadiabatic condition

One of the main practical problems in any kind of heat capacity data collecting software lies in the determination whether or not sample can be considered to be under semiadiabatic and equilibrium with surroundings conditions. This has to be established for at least certain duration of time before the heat pulse, which is long enough to collect sufficient number of temperature readings for a stable least squares fit (i.e. the points before $t_1$ in FIG. 8); and again for a certain time after the heat pulse. The correct solution of this problem ensures that the heat capacity would be measured at the highest possible precision. The second practical problem which needs to be solved when designing the calorimetric software is the precise determination of $t_2$ (i.e. the moment when sample's reaction to the introduced energy is accomplished, and the sample again comes in to equilibrium with the surroundings), because contrary to $t_1$, which is always known precisely, the moment $t_2$ will vary even for the same specimen with changing temperature (and obviously, it will be different from sample to sample) primarily because of the varying thermal conductivity.

Semiadiabatic and equilibrium conditions are characterized by a linear temperature versus time behavior of the calorimeter. This intuitive conclusion, however, needs some clarification, since it is obvious, that the liner versus time temperature rise (or drop) can not exist indefinitely long, even assuming that the temperature of surroundings do not change. By definition, the state of thermal equilibrium is characterized by the constant (time independent) heat leak between the surroundings and the calorimeter. Let us assume that the heat capacity of calorimeter is $C_c$. From now on calorimeter means a sample/sample holder assembly with any substance placed between sample and sample holder designed to improve a thermal connection between both. Assume also that during the period of time dt there is a heat leak dq between calorimeter and surroundings. Taking into account Eq.1 we now may write an equation for a time dependent temperature (T) behavior of the calorimeter;

$$\frac{dT}{dt} = \frac{1}{C_c} dq \qquad (6)$$

Rearranging and integrating (6) with respect to time we obtain:

$$T = dq \int \frac{1}{C_c} dt + T_0 \qquad (7)$$

since dq is a time independent constant. Note, that when dq>0, then the heat leak is positive and it is negative when dq<0. The exact integration of right hand part of Eq.7 requires knowledge of calorimeter's heat capacity behavior versus time, which is in general unknown. For a small temperature change, i.e. when $|dT|<<T$, which is typical for semiadiabatic conditions, it is possible to assume that $C_c(T+dT) \cong C_c(T)$ and this assumption becomes more accurate with higher temperature because of the tendency of the heat capacity to saturation at approximately 3R, where R is a universal gas constant (R=8.314 J/mol K). Therefore, we can introduce the further simplification, that for a limited time under semiadiabatic and equilibrium conditions when heat leak, dq, is small (i.e. $C_c>>dC$, where dC is total heat capacity change due to temperature change dT) the calorimeter's heat capacity is time independent. Hence, after integration the linearity of Eq.7 becomes straightforward:

$$T \cong \frac{dq}{C_c} t + T_0 \qquad (8)$$

Here $dq/C_c$ and $T_0$ are constants, time (t) is an independent variable, the temperature (T) is a dependent variable, and $T_0$ represents calorimeter's initial temperature when t=0.

It follows from Eqs. 7 and 8, that to achieve the conditions which are closest to adiabatic it is necessary i) to reduce heat leaks (dq) by improving the thermal insulation and adjusting the temperature of surroundings as close to the temperature of calorimeter as possible, or ii) to increase the calorimeter's heat capacity ($c_c$), or iii) both. It is also obvious, that it is easier to do so when temperature rises, since calorimeter's heat capacity naturally rises too. Another important note should be made at this point about microcalorimeters: since their heat capacities are extremely small, then more strict conditions apply to the quality of their thermal insulation. This is also true for a small sample calorimeters at the lowest (liquid helium and below) temperatures.

Returning to the beginning of this section, whenever (before or after the heat pulse) the temperature of the calorimeter behaves linearly, or almost linearly with time, then such a calorimeter can be considered as being in the semiadiabatic and equilibrium state. Usually, for the majority of calorimeters, described in the literature, it has been a-priori assumed, that linearity of calorimeter temperature behavior before the heat pulse (the so-called fore period) does not require special handling, since the calorimeter is always in the state of thermal equilibrium with a surroundings without an energy input from the sample heater. The question is in, for how long such pseudo-equilibrium state is in true semiadiabatic equilibrium condition? (see Eq.7). When calorimetric experiments were not automated, the calorimeter's temperature usually was recorded on XY-recorders as T vs. t plots, and it was relatively easy to distinguish the linear region before the heat pulse, and to establish when the linear behavior occured after the heat pulse using just human eyes and experience. With the beginning of automatization of the measurements, a different computer systems were used to monitor calorimeter temperature. It was standard practice, that the calorimeter temperature was measured for certain (predetermined) time intervals between each reading, usually 10–15 times and then a least squares fit was employed to determine the straight line (T=f(t)) parameters. Furthermore, determination of the moment of time $t_2$ (FIG. 8) was usually handled through the establishment of a certain time delays (wait periods) after the heat pulse and the linearity of the after pulse temperature behavior was automatically assumed after waiting time has expired. Usually the temperature reading delays before and after the heat pulse are chosen to be the same. Unfortunately, such "experimental settings" are arbitrary and had to be established by a trial and error procedure for every sample because of differences in thermal conductivity. Such an approach works relatively well only for the cases when heat capacity has been measured over a limited (and typically low, <~50K) temperature range. It is obvious, that for a large temperature spans (from liquid helium temperature and up to room temperature and above) thermal conductivity behavior of calorimeter changes drastically. For instance, thermal conductivity of pure copper at 4.2K initially rises by a factor of 4 at 20K and then drops by a factor of more than 10 from its peak value for T>100K. The behavior of another commonly used sample holder material—sapphire, is even worse: initially it rises by a factor of almost 300 (!) and then drops somewhat, remaining approximately 10 times higher at room temperature than at 4.2K. These changes are nonlinear functions of temperature, and are not known a-priori for the material being measured. All this makes the usage of manually adjustable pulse- and time-delays worthless when designing an automated calorimeter for a large (~4.2 to ~300K) temperature spans.

Formalization procedure

A formalization of the problem: whether or not calorimeter temperature varies linearly with time is based on a following consideration. Since T=f(t) is supposedly a linear function of time, then a first derivative of this function with respect to time has to be a constant. Or in the other words; when T=a+bt, then $$\frac{dT}{dt} = a = const. \qquad (9)$$

And when one fits a first derivative of temperature with respect to time versus time to a straight line, then this straight line has to have a zero slope. Unfortunately, the strict condition that the slope of the derivative equals zero can not be used as a sufficient formal criteria of temperature linearity versus time, because both time and calorimeter temperature measurements are always affected with at least random errors. One possible solution is to choose a certain small value as a zero-value threshold and when derivative's slope falls below it, then assume that the condition of Eq.9 is met. Nevertheless, any preset small value will again work only for a limited temperature interval, since the sensitivity, and therefore, the precision of the thermometry varies with temperature (see below). However, the random nature of temperature sensor and time measuring errors (we assume, that any serious systematic errors have been eliminated by using a proper thermometer and a well calibrated clock) may be rather helpful in this particular case, and allow us to propose a more elegant solution which is independent of a randomly chosen "preset small" values.

Consider the following: an array of derivatives of temperature with respect to time ($dT_i/dt_i$, for i=1, 2, . . . , n, where n is the number of temperature measurements) is used to determine the least square parameters (A and B) of the appropriate straight line $$A + B \times t_i = \frac{dT_i}{dt_i} \qquad (10)$$

where A is the derivative intercept and B is the derivative slope. Simultaneously, a standard uncertainty of both least square parameters A and B ($\sigma A$ and $\sigma B$, respectively) can be determined. As noted above, rather than compare a derivative's slope with a randomly chosen, predetermined small value to establish whether or not the former is close enough to zero, we now may use a standard uncertainty of the slope as a criteria of its zeroness in a following way:
when $$B \leq N \times \sigma B, \text{ then}$$

$$B \approx 0 \quad (11)$$

where N is a constant value. Therefore, we propose to replace a preset, small and common for every measurement series "zero" value by another small value which is now a unique one for every series of temperature measurements, and which will vary automatically with changing temperature sensor sensitivity and accuracy. It is obvious, that the higher the precision of temperature readings, the smaller the uncertainty in slope determination and vice versa. We have chosen N=2 (which stays close to a 95% confidence interval, N=1.96), since it seems to work perfectly well with our hardware. However it may be changed and a proper selection of N should depend on the accuracy of the thermometer calibration, and the temperature and time readings. It is also obvious that higher N will permit less "linear" T vs. t curves to qualify as formally linear, and vice versa.

Figure 9:
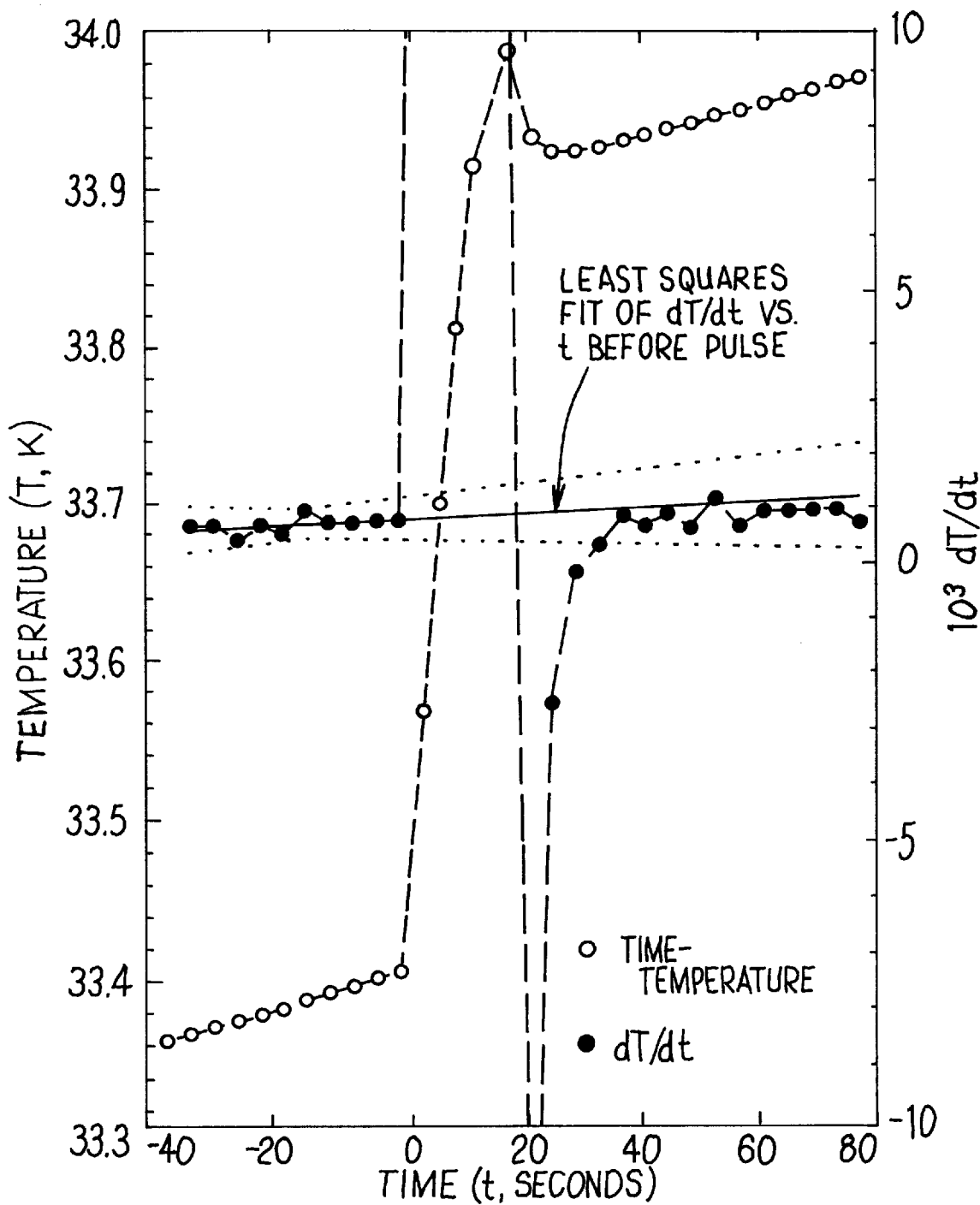
Figure 10B:
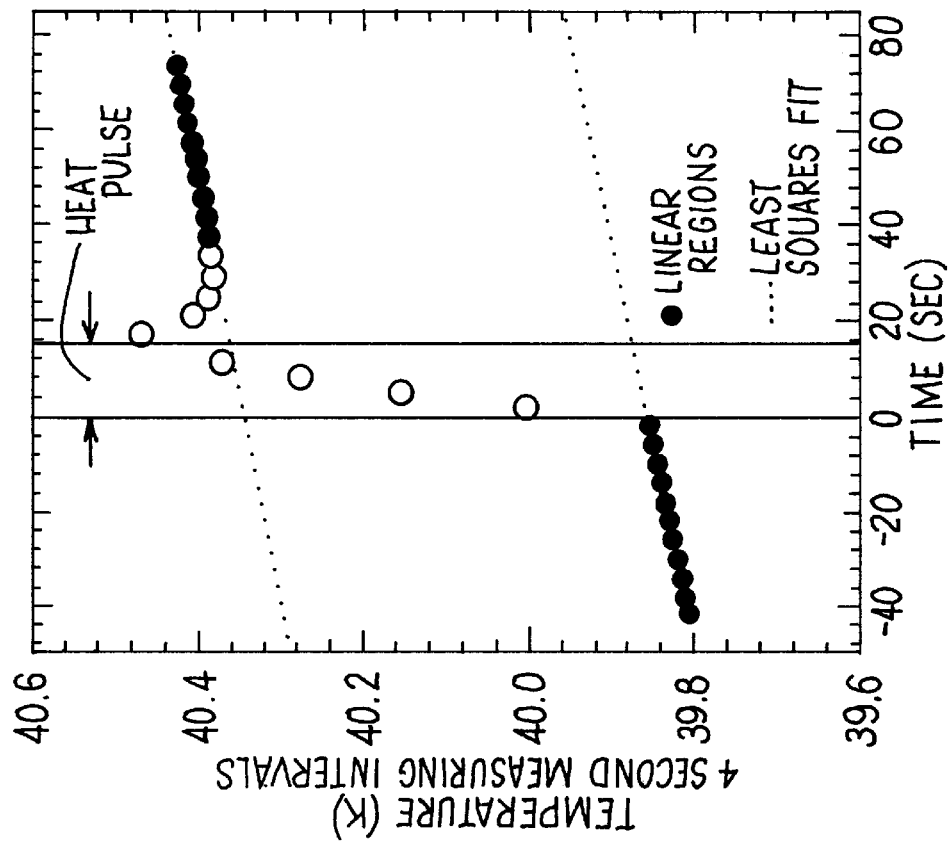
FIG. 10a is an after pulse relaxation time-temperature diagram and FIGS. 10b, 10c, and 10d are time-temperature heat-pulse diagrams.
Figure 10A:
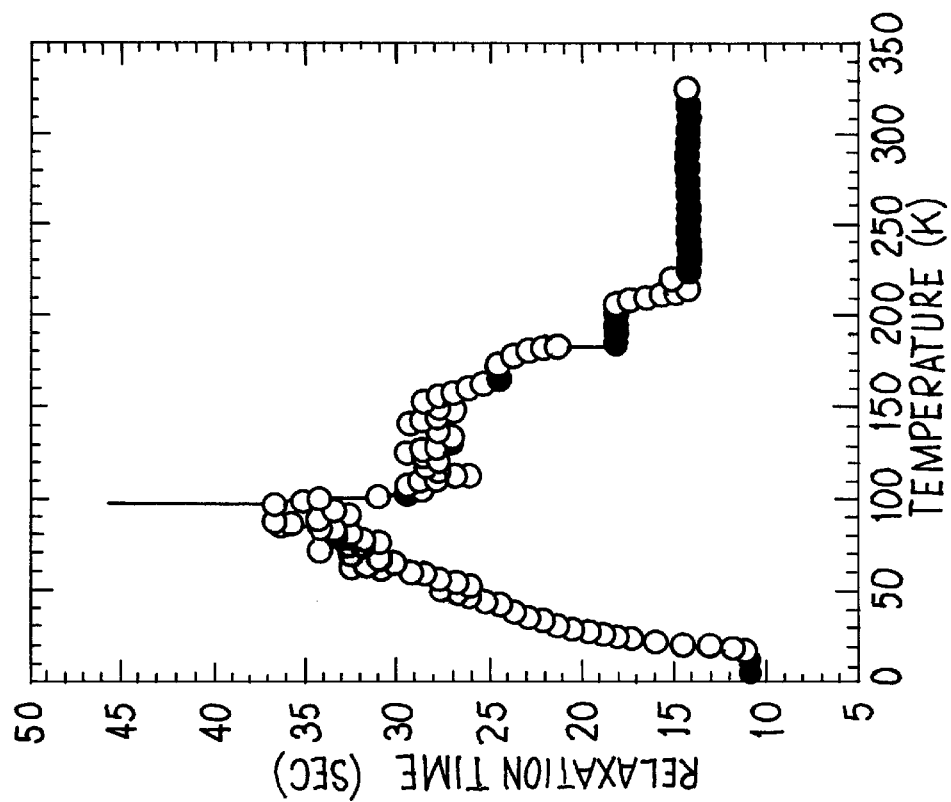
Figure 10D:
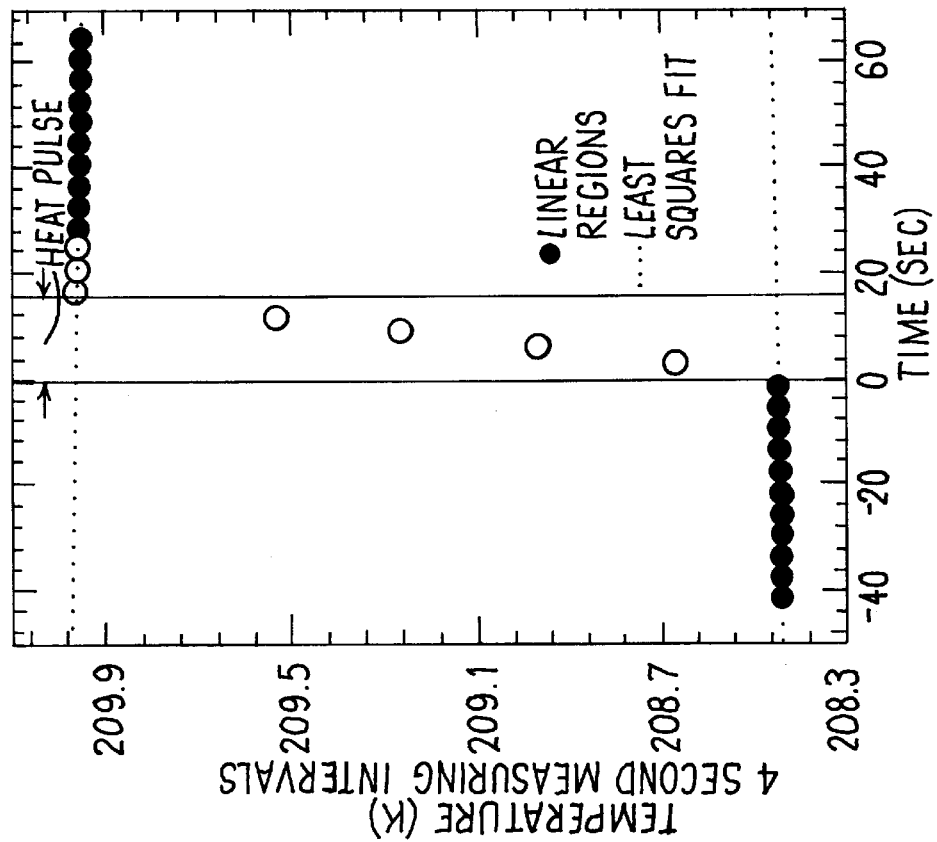
Figure 10C:
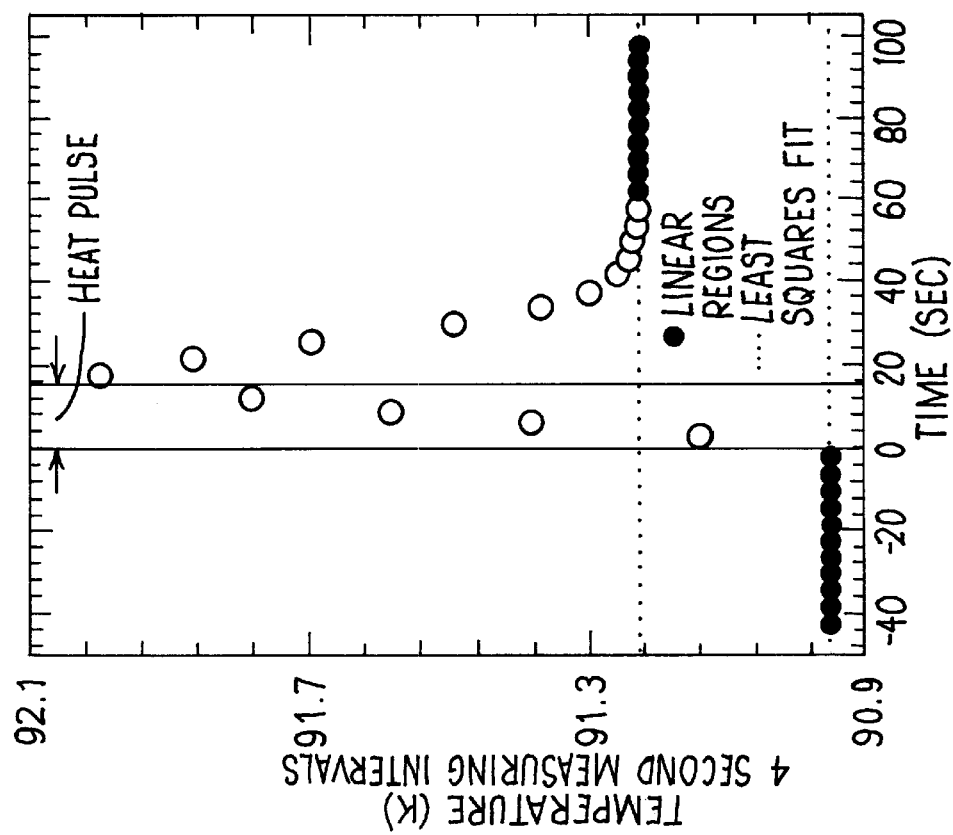

Now a whole cycle of taking one heat capacity data point using the developed formalization procedure will be considered in more details. FIG. 9 displays the same real time-temperature diagram as shown on FIG. 8, together with a derivative curve (i.e. dT/dt derivative curve). It is obvious, that before introducing any energy to the calorimeter (i.e. before the heat pulse) the presence of semiadiabatic and equilibrium conditions has to be detected. We have chosen, that at least 10 consecutive temperature readings should satisfy conditions, described above (Eqs.8–10). Then, data collection software starts a heater to introduce a predetermined amount of energy into the calorimeter, which causes a sharp rise of calorimeter's temperature. The problem which requires solution after the pulse has been terminated is—to determine as precise a s possible when the introduced energy is evenly distributed through the calorimeter, that is: when the calorimeter's temperature again shows a linear with time behavior. A simple continuation with monitoring the dT/dt vs. time curve slope to satisfy Eq.11 conditions is not enough, because the derivative curve usually goes through a maximum and then a minimum (see FIG. 9), and their presence may cause the computer to include these values, accidentally making σB very large and thus non-zero derivative slope would be mistakenly accepted as close enough to zero. However, a simple consideration, recalling that temperature of the surroundings does not change much during the short heat pulse (10–20 seconds), and that calorimeter temperature usually rises during determination and vice versa. We have chosen N=2 (which stays close to a 95% confidence interval, N=1.96), since it seems to work perfectly well with our hardware. However it may be changed and a proper selection of N should depend on the accuracy of the thermometer calibration, and the temperature and time readings. It is also obvious that higher N will permit less "linear" T vs. t curves to qualify as formally linear, and vice versa.

Now a whole cycle of taking one heat capacity data point using the developed formalization procedure will be considered in more details. FIG. 9 displays the sa me real time-temperature diagram as shown on FIG. 8, together with a derivative curve (see FIG. 9 caption for details). It is obvious, that before introducing any energy to the calorimeter (i.e. before the heat pulse) the presence of semiadiabatic and equilibrium conditions has to be detected. We have chosen, that at least 10 consecutive temperature readings should satisfy conditions, described above (Eqs.8–11). Then, data collection software starts a heater to introduce a predetermined amount of energy into the calorimeter, which causes a sharp rise of calorimeter's temperature. The problem which requires solution after the pulse has been terminated is—to determine as precise as possible when the introduced energy is evenly distributed through the calorimeter, that is: when the calorimeter's temperature again shows a linear with time behavior. A simple continuation with monitoring the dT/dt vs. time curve slope to satisfy Eq.11 conditions is not enough, because the derivative curve usually goes through a maximum and then a minimum (see FIG.9), and their presence may cause the computer to include these values, accidentally making σB very large and thus non-zero derivative slope would be mistakenly accepted as close enough to zero. However, a simple consideration, recalling that temperature of the surroundings does not change much during the short heat pulse (10–20 seconds), and that calorimeter temperature usually rises during that heat pulse, leads to the conclusion that dq term from Eq.7 should decrease due to Newton's law of cooling. Together with usual increase of the calorimeter's heat capacity ($C_c$) this means that the slope of the equilibrium temperature behavior after the pulse must be approximately equal and slightly lower than the same before the pulse. And again the "approximately equal and lower" criterion can easily be used while detecting equilibrium conditions visually (see FIG. 9), it does not work as a formal criterion necessary for complete automation. Nevertheless, it is possible to use the random temperature and time measurement errors once more to establish a formal criteria of approximate equity of slopes before and after the heat pulse. We can always extrapolate before the pulse T vs. t slope from the derivative's straight line parameters A and B (Eq.10), which is shown as a solid line on FIG. 2, to after the pulse region, and use the estimated σA and σB to determine the confidence intervals of extrapolation as follows: since E=A+B×t, then $$\sigma E = \sigma A + \sigma B \times (t-t)$$

where t represents the midpoint of the before pulse time for all observations used in the least squares fit. Here E and σE are extrapolated from the before pulse linear region T vs. t slope and its standard uncertainty, respectively. The dotted lines in FIG. 9 show an area within E±2σE interval, which again approximately corresponds to a 95% confidence interval. Therefore, the proposed formal criterion is as follows: as soon as the after pulse dT/dt values begin to fall within E±NσE interval, it is safe to conclude that calorimeter has come close to thermal equilibrium with the surroundings and as soon as following 10 consecutive temperature readings satisfy the condition of linearity of $T_{after}$ vs. t behavior (Eq.11), the after pulse measurements are over. Time $t_2$ corresponds to the first of those 10 consecutive readings when sample is detected to be again in equilibrium with its surrounding conditions after the pulse.

Certainly, the chosen formalization parameters discussed above (10 consecutive data points and agreement within ±2σ) can be changed and adjusted dependending on the actual calorimetric hardware. One has to remember, however, that usage of the suggested criterion is based on standard uncertainties, determined from the least squares. The least squares uncertainties (a) are inversely proportional to square root of number of observations (n) less number of independent least squares parameters (m), i.e.

$$\sigma \propto \frac{1}{\sqrt{n-m}}.$$

Therefore, particular care should be taken that standard uncertainties are not overestimated, i.e. number of observations has to be significantly higher than number of independent variables. In our case, we have chosen 10 observations to determine 2 independent least squares variables, and this probably can be considered as a sufficient lower limit.

The FIG. 10 illustrates how the developed formalization algorithm works in practice. The results were obtained while measuring the non-magnetic heat capacity of a solid state electrotransport purified polycrystalline Dy sample. It is well known, that ferromagnetic Dy undergoes magnetic and structural first order phase transitions at 91K on warming and remains antiferromagnetic up to 180K, where the second order antiferromagnetic to paramagnetic phase transition occurs. It is obvious from FIG. 10a, that in the ferromagnetic state, the thermal conductivity of calorimeter (the copper sample holder plus a piece of the Dy-metal weighting 1.2238 g) is lowered by approximately a factor of four (i.e. the internal thermal relaxation time increases from approximately 11 to approximately 45 seconds). FIG. 10b shows the time-temperature profile of a typical data point in the ferromagnetic region. The longest relaxation time was required at the temperature where ferromagnetic to antiferromagnetic transition occurs, FIG. 10a and 10c. As soon as Dy becomes antiferromagnetic, thermal conductivity improves sharply and stays almost unchanged until antiferromagnetic to paramagnetic transition occurs at approximately 180K. Then again another step-like lowering of relaxation time occurs and it remains almost unchanged up to room temperature. An example of the time-temperature behavior in the paramagnetic region for Dy is shown in FIG. 10d. At this point we would like to stress that all the significant changes in the thermal relaxation behavior of the calorimeter, containing sample of polycrystalline dysprosium were processed automatically by data collecting software using the described above formalization procedures. No human intervention occured and not a single parameter was changed during data collection. The visual analysis of shown in FIG. 10b, 10c, and 10d time-temperature profiles shows that the proposed algorithm works excellently.

It will be understood that the above description of the invention is susceptible to various modifications, changes and adaptations, and the same are intended to be comprehended within the scope of the appended claims.

We claim:

1. Apparatus for making a series of calorimetry measurements of a sample, comprising a sample holder in which a sample is disposed, a sample temperature sensor for measuring sample temperature in a foreperiod before and in an afterperiod after a sample heat pulse and a sample heater for providing said sample heat pulse, both in thermal connection with said sample, a heat shield in which the sample holder is positioned and including an electrical heat shield heater, electrical power supply means for providing respective electrical power pulses to said sample heater to generate respective sample heat pulses, and electrical power control means for adjusting, if necessary, the electrical power output of said heat shield heater, from one measurement to the next in response to a sample temperature-versus-time change determined by said control means in an afterperiod of a prior heat pulse to provide a sample temperature-versus-time change in a subsequent heat pulse that is indicative of the sample being in a thermal equilibrium state relative to its environment.

2. The apparatus of claim 1 wherein said electrical power control means comprises a dc current source and a computer control device that can vary said electrical power from said source to said heat shield heater incrementally in response to said sample temperature-versus-time change determined in said afterperiod of a previous heat pulse to provide said sample temperature-versus-time change in said subsequent heat pulse that is indicative of the sample being in thermal equilibrium state relative to its environment.

3. The apparatus of claim 1 wherein said electrical power control means adjusts said power to said heat shield heater to provide said sample temperature-versus-time change in said subsequent heat pulse that is substantially linear in the foreperiod and in the afterperiod of said subsequent heat pulse.

4. The apparatus of claim 1 wherein said temperature sensor comprises a thin film resistor on said sample holder and operable over a range of temperatures from about 3K to 350K.

5. The apparatus of claim 1 further including means for establishing a dc magnetic field about said sample holder for subjecting said sample to a d.c. magnetic field during said series of calorimetry measurements.

6. Method of making a series of calorimetry measurements of a sample, comprising disposing said sample in a heat shield including an electrical heat shield heater, providing respective heat pulses to said sample, measuring sample temperature in a foreperiod before and in an afterperiod after each heat pulse, determining a sample temperature-versus-time change for each heat pulse, and adjusting the electrical power output to said heat shield heater, as necessary, in response to the sample temperature-versus-time change determined in an afterperiod of a previous heat pulse to provide a sample temperature-versus-time change in a subsequent heat pulse that is indicative of the sample being in thermal equilibrium state relative to its environment.

7. The method of claim 6 including adjusting the electrical power output to said heat shield heater, as necessary, in response to said sample temperature-versus-time change determined said afterperiod of said previous heat pulse to provide said sample temperature-versus-time change in said subsequent heat pulse that is substantially linear in the foreperiod and in the after period of said subsequent heat pulse.

8. The method of claim 6 including measuring the temperature of said sample with a thin film resistor operable over a range of temperatures from about 3K to 350K.

9. The method of claim 6 further including establishing a dc magnetic field about said sample for subjecting said sample to a d.c. magnetic field during said calorimetry measurements.

10. The method of claim 6 where said series of calorimetry measurements involves making a series of heat capacity measurements, calculated as $C=\Delta O/\Delta T$, where C is the heat capacity, $\Delta O$ is the heat supplied to a calorimeter by the sample heater during the heat pulse and $\Delta T$ is the subsequent increase in calorimeter temperature.

* * * * *